United States Patent [19]

Puchy

[11] Patent Number: 4,887,756
[45] Date of Patent: Dec. 19, 1989

[54] SURGICAL STAPLER PROVIDING VARIABLE DEGREE OF STAPLE CLOSURE

[76] Inventor: David P. Puchy, P.O. Box 382, Epping, N.S.W. 2121, Australia

[21] Appl. No.: 186,706

[22] Filed: Apr. 21, 1988

Related U.S. Application Data

[63] Continuation of Ser. No. 826,869, Jan. 7, 1986, abandoned.

[30] Foreign Application Priority Data

May 7, 1984 [AU] Australia .............................. PG4869

[51] Int. Cl.⁴ ............................................ A61B 17/00
[52] U.S. Cl. ...................................... 227/19; 227/88; 227/89; 227/90; 227/148; 227/901
[58] Field of Search .................... 227/DIG. 1, 19, 88, 227/89, 90, 142

[56] References Cited

U.S. PATENT DOCUMENTS

| | | | |
|---|---|---|---|
| 2,707,783 | 5/1955 | Sullivan | 227/DIG. 1 |
| 3,082,426 | 3/1963 | Miles | 227/DIG. 1 |
| 3,314,581 | 4/1967 | Kapitanov et al. | 227/142 |
| 3,641,652 | 2/1972 | Arnold et al. | 227/142 X |
| 3,873,016 | 3/1975 | Fishbein | 227/DIG. 1 |
| 3,973,709 | 8/1976 | Akopov et al. | 227/DIG. 1 |
| 4,327,485 | 5/1982 | Rix | 227/142 X |
| 4,375,866 | 3/1983 | Giersch et al. | 227/DIG. 1 |
| 4,391,401 | 7/1983 | Moshofsky | 227/19 |
| 4,399,810 | 8/1983 | Samuels et al. | 227/19 X |
| 4,411,378 | 10/1983 | Warman | 227/19 |
| 4,471,897 | 9/1984 | Genyk et al. | 227/89 X |
| 4,477,007 | 10/1984 | Foslifen | 227/19 |
| 4,489,875 | 12/1984 | Crawford et al. | 227/19 |
| 4,493,322 | 1/1985 | Becht | 227/DIG. 1 |
| 4,527,725 | 7/1985 | Foslien | 227/19 |
| 4,542,844 | 9/1985 | Olesen et al. | 227/88 X |
| 4,558,810 | 12/1985 | Mulhauser et al. | 227/19 |
| 4,582,237 | 4/1986 | Storace et al. | 227/19 |

FOREIGN PATENT DOCUMENTS

| | | |
|---|---|---|
| 6872881 | 12/1981 | Australia . |
| 8569282 | 1/1983 | Australia . |
| 1127983 | 8/1983 | Australia . |
| 576818 | 5/1933 | Fed. Rep. of Germany . |
| 8401706 | 5/1984 | PCT Int'l Appl. . |

OTHER PUBLICATIONS 270981 4/1982, Australia.

Primary Examiner—Paul A. Bell
Attorney, Agent, or Firm—Pravel, Gambrell, Hewitt, Kimball & Krieger

[57] ABSTRACT

A magazine fed, trigger driven surgical stapler to close a surgical incision. The stapler has an anvil and a staple driving die, an adjustable stop for controlling movement of the staple driving die so that staples can be reformed to a range of closed positions. The anvil is pivotable under control of the staple driving die between a staple engaging position and position clear of the staples. A forcep assembly operable under actuation control of the staple driving die acts to draw the edges of the incision into close approximation. A staple blank with a concave back, upper arms extending the concave shape of the back and pointed lower arms extending downwardly and inwardly from the upper arms, which blank on reformation around the anvil will adopt a substantially hexagonal configuration.

33 Claims, 19 Drawing Sheets

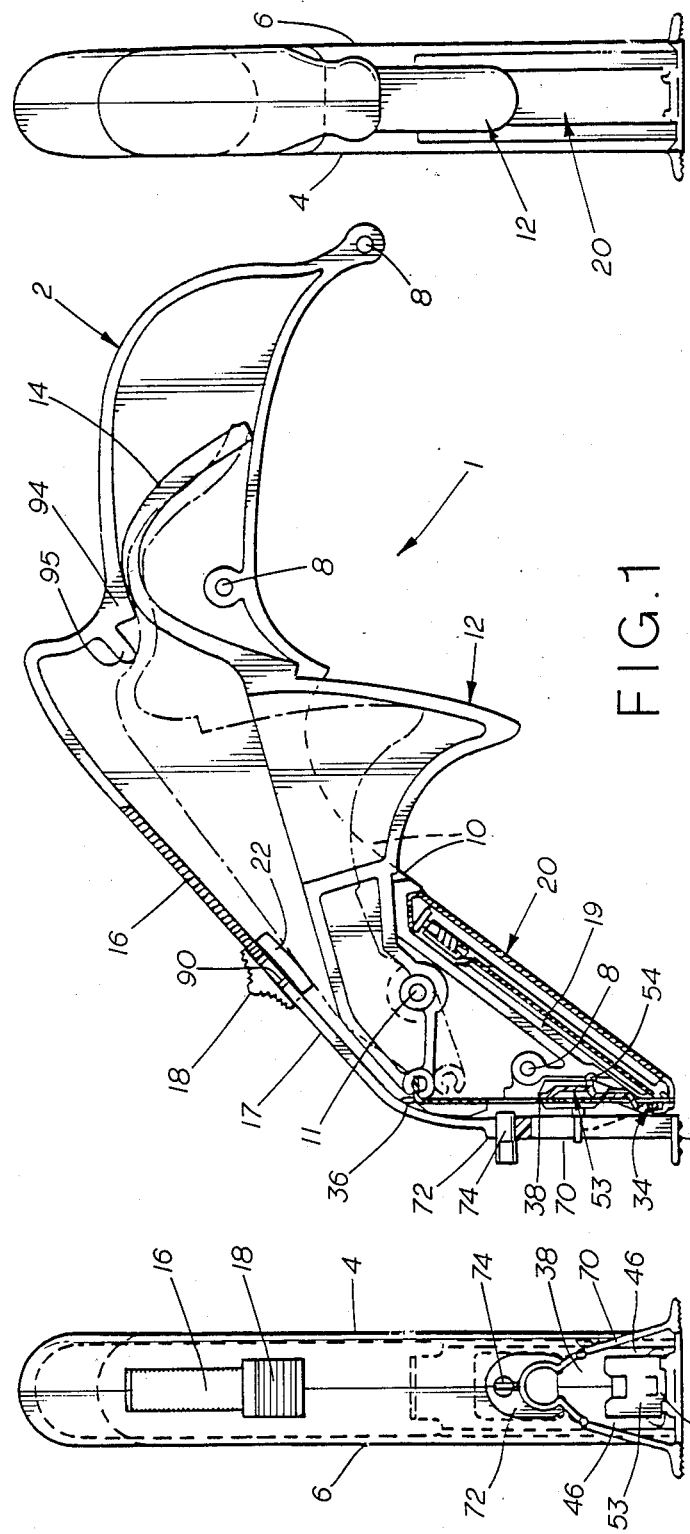

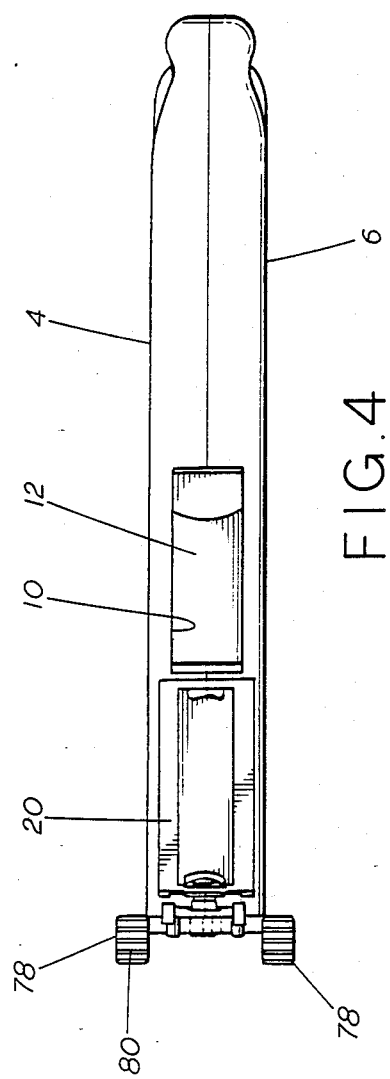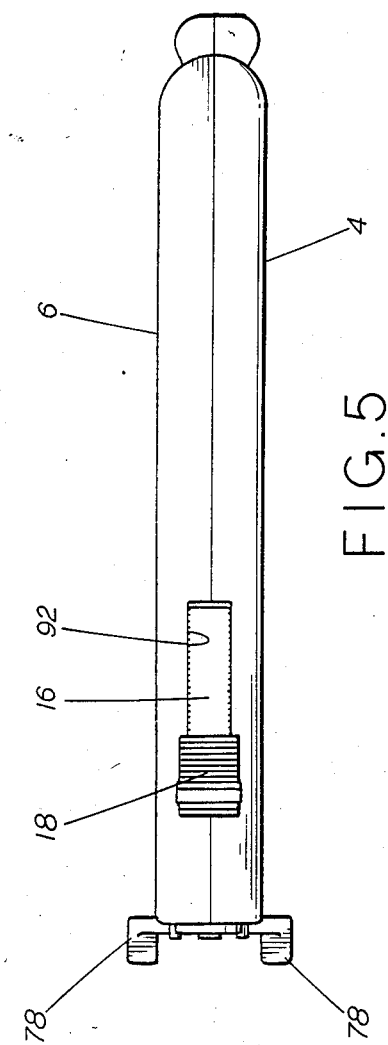

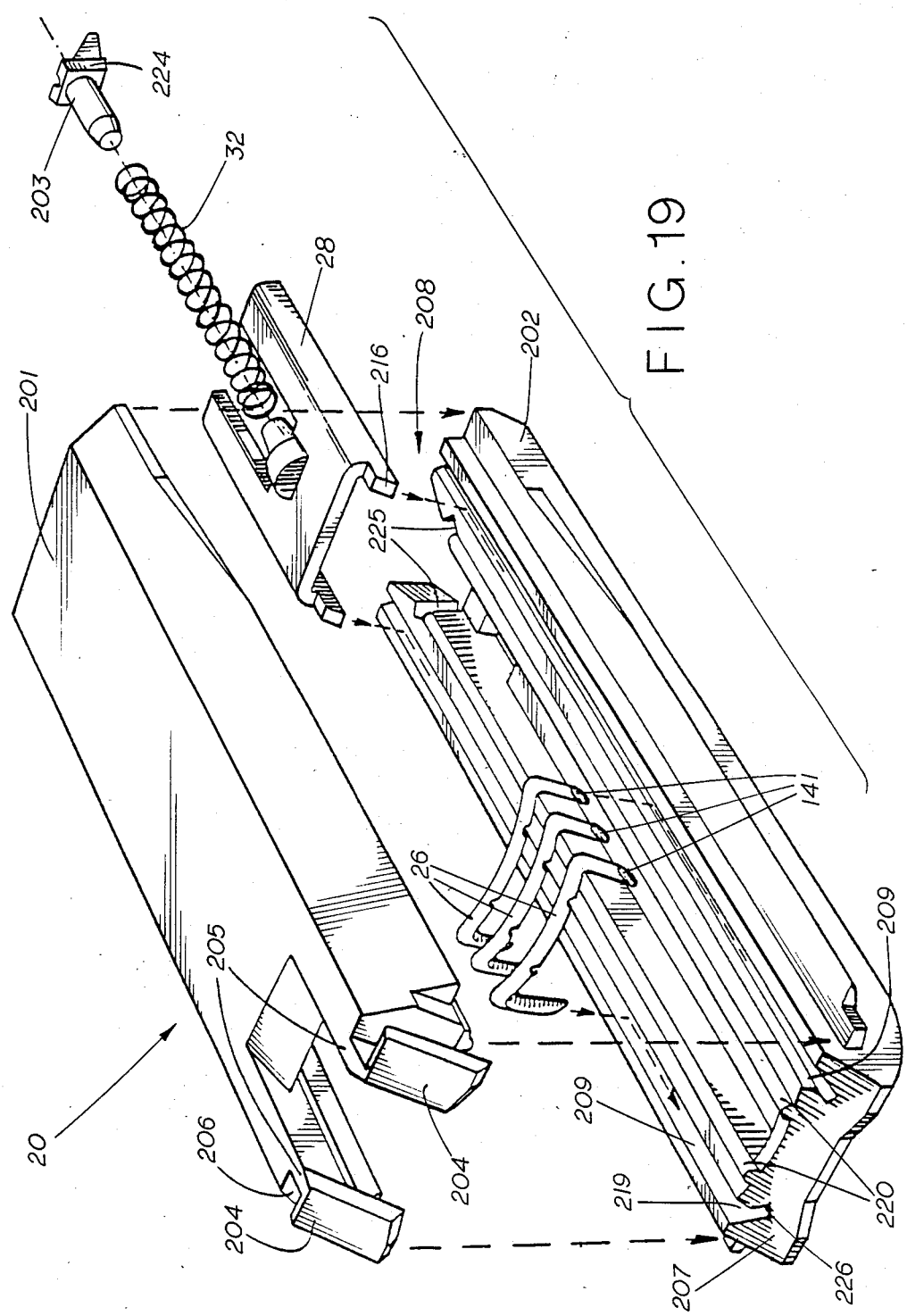

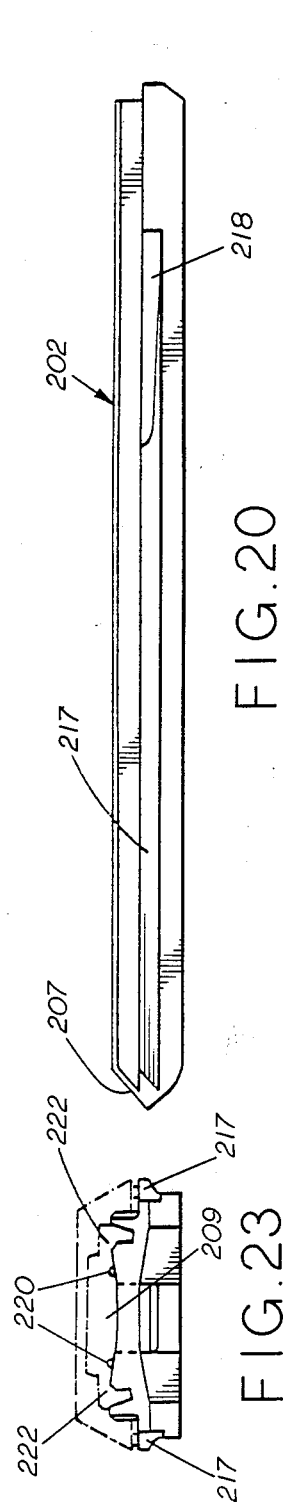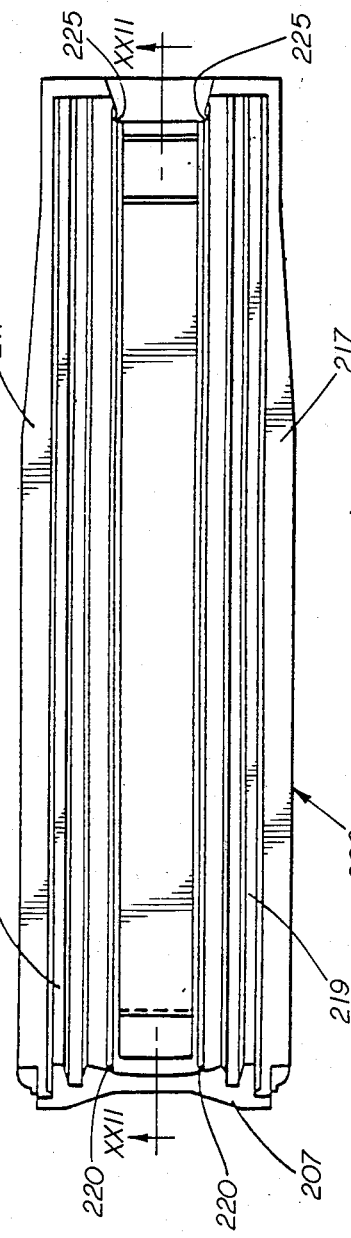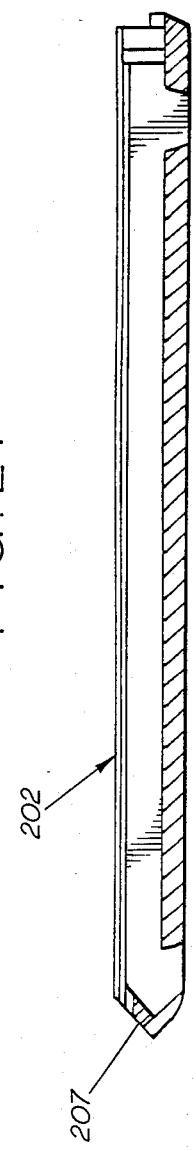

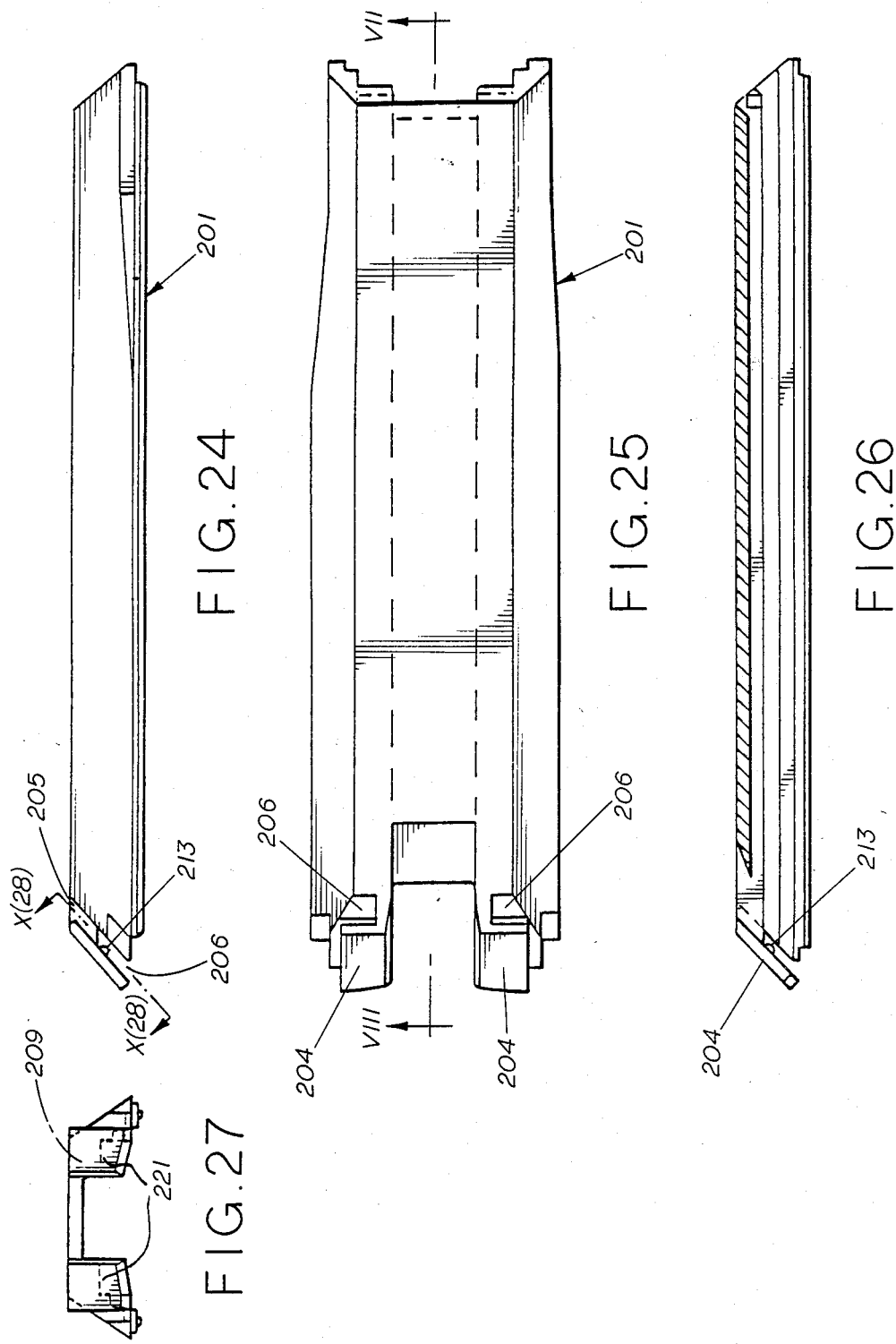

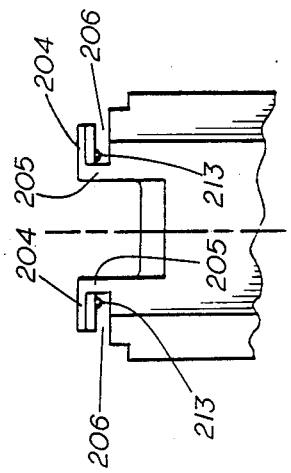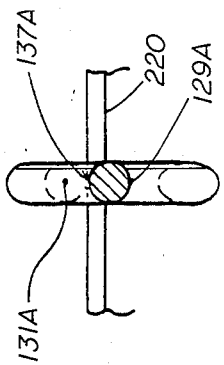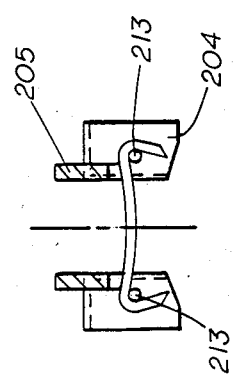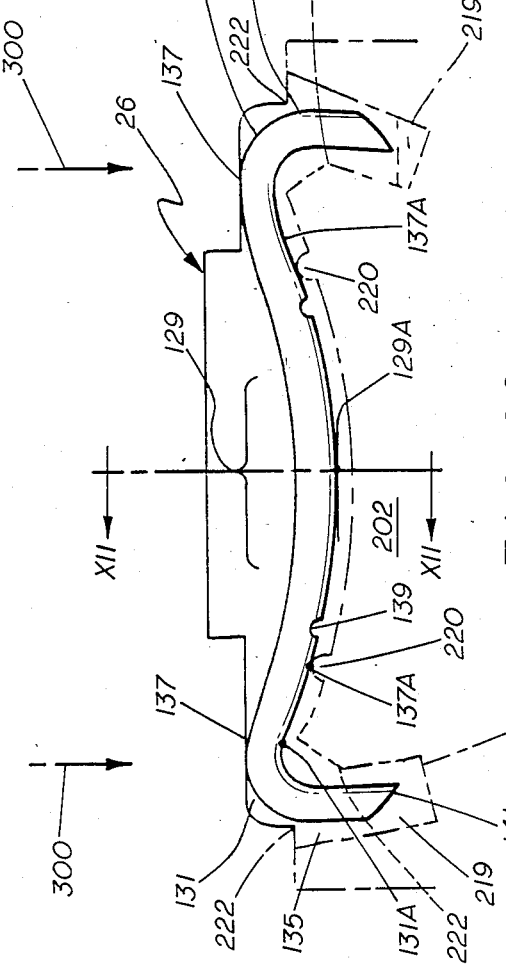

SURGICAL STAPLER PROVIDING VARIABLE DEGREE OF STAPLE CLOSURE

CROSS-REFERENCE TO RELATED APPLICATION

This is a continuation of U.S. Pat. application Ser. No. 826,869 filed Jan. 7, 1986 now abandoned.

BACKGROUND OF THE INVENTION

The present invention relates to improvements in disposable surgical skin stapling devices and the staples themselves, including a method of wound closure and a means of inserting the improved staple to secure the wound closed in proper apposition.

It is mainly for reasons of the difficulties encountered in achieving good wound apposition; avoiding inversion in at least part of the wound, and (the lack of) control to close up or minimize excessive resulting eversion, that many surgeons will not use or have discontinued to use skin stapling devices of the known art for wound closure procedures. Instead, they prefer to relay on their skills with the time honored though more laborious suturing procedure.

When using sutures to secure a wound closed, the surgeon is able to manipulate the wound or incision somewhat, stopping during the tying of each suture if necessary to re-appose edges or faces that may have fallen away and also tightening his knots to achieve just the degree of eversion he desires.

The surgeon is aware of the importance of preventing a closed wound inverting (i.e. the opposing faces of the skin separate below and/or between the points at which they are secured together). This can occur with sutures and staples alike if care is not taken to guard against it. When a wound inverts, it forms a subcutaneous pocket or crevice into which the blood or plasma leaks from surrounding capillaries and in which infection can occur. Thus, in order to guard against this risk, the surgeon deliberately compensates by closing the wound or incision in an everted form (i.e. the opposing faces of the wound are allowed to fall away from each other, substantially towards the epidermis or skin surface). In an everted closure, any appearance of blood or plasma is open to view and the progress of healing can be monitored during daily inspection or re-dressing.

Wound healing takes place from the inside to the outside (i.e. from the subcutaneous layers to the epidermis). As healing progresses towards the epidermis, scar tissue is formed. It follows that the greater the eversion, the more scar tissue that will form. Scar tissue is undesirable for several reasons. Cosmetically, it is unpleasing; from a practical viewpoint, it is never as strong or as tough as the parent skin, tending to split and tear much more easily.

Thus it can be appreciated that the smaller the eversion, the less visible and stronger the healed wound will be. Conversely however, by minimizing wound eversion to reduce scar tissue formation, the surgeon increases the risk of creating inversion. It is the acquired skill of the surgeon which enables him to achieve a balanced closure.

It is apparent that the ideal would be to have the opposing faces of the wound closed together in perfect apposition from the subcutaneous to the epidermis with neither inversion or eversion (i.e., closed in perfect dermal and epithelial alignment). This is in fact what a cosmetic surgeon (or "plastic" surgeon) achieves by painstakingly apposing the closed wound and controlling it during securing, with very skillful suturing, using fine threads and needles. However, for the greater majority of wound closing procedures this time and care is unwarranted and unnecessarily costly Just as has to learn his skills in suturing a wound closed in an approved manner, so the surgeon also has to learn new skills when using staples for this same purpose. When closing any wound, it is common practive to insert a first retractor (commonly called a skin hook) in one end of the incision and a second retractor in the opposite end of the incision. The retractors are mutually aligned along the axis of the incision and drawn apart so as to elongate the incision. This action, usually performed by an assistant, tensions the tissue surrounding the incision sufficiently to approximate the edges of the incision and enables the surgeon to apply forceps to pinch the edges of the incision together while the suture or staple is inserted.

In my U.S. Pat. No. 4,753,237, I describe a retractor device for use with this invention for wound closures in general which obviates the need for an assistant using a first and a second retractor to approximate the wound.

If good apposition is achieved by the action of the first and second retractors, it is sometimes not necessary to use forceps to further pinch the edges together, when suturing the wound closed. A different technique is necessary when wounds or incisions are stapled.

When using staples of the conventional or known art type for wound closure, it is essential to pinch the edges together as described above in order to bridge the said edges with the staple which is inserted adjacent to the gripping forceps. Thereafter, the forceps are released and progressed along the incision to the approximate position chosen to insert the next staple, whereafter the stapling device is again operated. The surgeon operates the stapling device with one hand and the forceps with the other hand, while the assistant maintains the tension on the incision with the first and second retractors and this progress continues until the surgeon completes the wound closure.

It has become common practice with surgeons using conventional stapling devices of the known art, in situations when it proves difficult to grip the skin on both sides of the incision with the forceps (which is frequently the case) to hold the last inserted staple captive on the anvil within the stapling device and by raising the device upwardly away from the incision, use the inserted staple to draw up a ridge of skin along both sides of the incision, the said ridge being at its most elevated in relation to the patient's body, immediately beneath the said inserted staple, and tapering away towards the opposite end of the incision. This provides the surgeon with relatively good surfaces to grip with the forceps before releasing the said last inserted stable.

However, this practice is undesirable for several reasons. It can be appreciated that aggravation and elongation of the puncture holes in the skin by the inserted staple prongs frequently causes bleeding of the said puncture holes. While this in itself is not serious, and the amount of bleeding is minute, the additional scar tissue resulting, particularly when for one or another reason, the staples are left in for more than a few days, can make the difference between the puncture holes healing virtually without trace or leaving very noticeable 'dots' or 'snake eyes' astride the incision scar.

In addition, this practice can cause misapposition to that part of the wound already closed, thus increasing the difficulty of achieving good overall apposition alignment of the wound. This condition is most likely to occur when preceding staples are not particularly well aligned and when the staple clamping pressure of the preceding staples is not evenly distributed to the skin on opposing edges of the wound, leaving a 'fat' side and a 'thin' side. The effect of lifting or ridging the skin with the last inserted staple in this described circumstance is likely to cause the skin on the 'fat' side to be forced upwards along the vertical arm of the staple on that side, while the skin on the 'thin' side falls away leaving the opposing faces of the incision in an overlapped state.

However, possibly the most serious aspect of this practice is the one resulting from the additional tension exerted on the edges of the opposing faces of the incision at the epidermis. This said added tension results in the said edges turning inwards towards each other, particularly in areas of the patient's body where there is not much flesh or fatty tissue between the skin and the bone structure beneath. The effect of this is that it not only leads to inversion of the wound under the clamping action of the succeeding staples, which in all probability will be detected by the surgeon and avoided, but that it will cause separation of the opposing faces in the subcutaneous region in the area already closed, with the possibility that an undetected inversion may remain even when the skin is lowered and the staple released from the stapling device.

One further serious effect which result from this practice is that the degree of ridging of the skin preparatory to inserting the following staple is usually excessive. When excessive in relation to the ratio of the height of the ridge to the width of the ridge (when the skin is 'thin' on both sides of the incision) the fall away on release of the staple results in excessive eversion of the wound; while, when the ridging is excessive in relation to the skin being 'fat' on both sides of the incision, the clamping pressure compressing the two sides together can result in damaged tissue with permanent ridging and staple bridging marks remaining after the incision has healed, particularly when for reasons of slow healing (or other) all the staples are not removed from the wound within the space of three (3) to six (6) or seven (7) days after the operation.

Further shortcomings of the conventional staple will become apparent from the ongoing text. Irrespective of the technique used by the surgeon in gripping together the edges of the opposing sides of the incision preparatory to inserting the following staple, on many of a patient's body, especially surfaces which slope away from the effective perpendicular axis of the gripping forceps and/or long wounds, it is almost impossible for any surgeon to mass the same amount and shape of skin tissue (if viewed in cross section) on both sides of the incision. Invariably one side is 'fat' and the other is thin and as described above, this results in excess eversion of the closed wound and/or overlapping.

It is often difficult if not impossible to get grip and purchase with forceps on the skin on the lower side of an incision on sloping skin surfaces, and the 'fat' and 'thin' condition described above is the best result that can be expected. When this condition is considered in the light of the almost certain probability that the stapling device will not be perfectly aligned in relation to the axis of the incision, and/or that it will be tilted slightly off a plane rising perpendicularly from the axis of the incision; in addition to which most stapling devices of the known art do not possess a mechanism to accurately centralize the staple in line with the reforming die within the said stapling device; and when considered further in the light of the bending action of staples of the known art or conventional form (which will be described further on in this text) and in particular, the path followed by the points of the said staple during reformation when the said points puncture and penetrate into the skin, gathering up and carrying the said skin inwards and upwards, it can readily be seen and appreciated that the possibility of obtaining good wound apposition and alignment is very slim indeed. It has been observed in fact, that contrary to achieving good apposition, the penetrating action of the staple often upsets the degree of apposition of the opposing faces already obtained with the forceps in pinching the said opposing faces together.

Such stapling devices as noted above all perform this function in the same basic manner irrespective of the variations in physical appearance of the said stapling devices; and most use the conventional channel shaped staple form, reformed by the die means and inserted into the skin of the patient astride the incision, and in so doing, closing into a substantially rectangular configuration. Most of the said stapling devices follow the same basic format, commonly possessing a clip of staples, a guide along which the staples are fed to an anvil, which is commonly of a fixed arrangement and frequently formed on one end of the said guide, the said staple then being reformed around the said anvil by means of a rise and fall die actuated by a linkage via finger or hand pressure. As stated above they are not in practice, easy to use. While at least two of the known commonly used stapling devices utilize mechanisms to ensure positive release of the said staple from the said stapling device following insertion of the said staple, the others of fixed anvil design do not. In order to free or release the staple from the anvil over which it has been or reformed, it is necessary for the surgeon to move the said stapling device in either a forward or rearward direction, depending upon the configuration of the particular stapling device. In hospitals where both types are used, this is an unnecessary confusion and nuisance for the surgeon.

The outward or physical appearance of the body casing of the commonly used stapling devices varies, some a little, some considerably from each other, but usually follow a style suitable for one or the other of two hand actions—either a pistol grip with trigger finger operating the actuating mechanism, or a palm grip with all the fingers enclosing around and squeezing a lever to operate the actuating mechanism, similar to the grip and action of a pair of pliers. These two types are further subdivided into two groups; those orientated for use in a substantially vertical plane and those which are used in a substantially horizontal plane. A further variation of the former orientation is one of a palm grip arrangement where articulated elbows extend from two opposite sides of an elongated body, said elbows being squeezed between the palm and fingers to operate the actuating mechanism.

Of all the known art skin stapling devices commonly in use, possibly the most convenient and comfortable to use is one having a pistol grip configuration. However, it suffers from the considerable disadvantage that the trigger and handle are too close to the patient's wound when in the operating position. This causes interference with the wound and also interference between the surgeon's hand holding the stapling device, and the assistant's hand holding the skin retracting device.

Many of the known art skin stapling devices commonly in use suffer from the further design disadvantage of partially or fully enclosed body casings surrounding the region of staple exit. This prevents the surgeon from sighting the staple points as the said staple begins to deform prior to penetrating the patient's skin. Surgeons find it preferable to align and position the said stapling device by sighting the acutal staple points, rather than relying on some centerline marking on the body casing of the said stapling device.

One further disadvantage of most of the known art skin stapling devices commonly in use is that the body casing design surrounding and adjoining the staple exit and in proximity to the staple exit, is such that it obscures the wound from the surgeon's line of vision, while the underside of the said body casing sits on the previously inserted staples, all of which makes it difficult for the surgeon to judge the spacings between succeeding staples.

The majority of commonly used staples mentioned above, are of the conventional 'channel' configuration, such staples consisting of a substantially straight back portion at either end of which is located an elbow region, each of the said elbow regions folding in a downwards direction and leading to a prong extending therefrom, and each such prong forming forming an included angle with the said back portion of the said staple of approximately 90°, each said prong having a sharpened point formed on its end, opposite the elbow region.

The back portion of the formost said staple fed from the clip or magazine, is located substantially symmetrically astride the anvil underlying the staple deforming die, with the prongs pointing in a downwardly direction. When acted upon by the said die, the said back portion of the said staple is folded over each side edge of the said anvil, also in a downwardly direction, the said folding causing the formation of shoulder regions which are separated from the elbow regions by straight portions (which were formerly part of the back portion) and which will now be referred to as forearm portions.

Some of the known stapling devices in common use provide a means for minimizing the bowing effect on the back portion of the deforming staple, thus maximizing the bending in the shoulder region and limiting spring-back when the deforming die is withdrawn.

At least one manufacturer of conventional staples also pre-crimps the inside surfaces of the back portion in order to more accurately confine the bending to the crimped regions, which are the shoulder regions. This method is also effective in minimizing spring-back at the bends.

During deformation by the die, the prong portions of the staple rotate through approximately 90° changing from a substantially vertical plane to a substantially horizontal plane. The points of the prongs commence to penetrate and gather up the tissue on the side slopes of the ridged up wound usually somewhere between 30°–45° of rotation. It can be appreciated that in continuing to rotate to a horizontal plane, the said penetrating prongs will cause the tissue surrounding the penetrations, as well as that tissue above the said penetrations, to be elevated in relation to its former plane. It is the geometrical effect of the rotation of the said prongs which works adversely in combination with the other undesirable characteristics of this procedure, described in the foregoing text, which frequently spoils and wound apposition.

One further limitation of the said conventional staple is that it cannot be adjusted (if so desired) beyond the design limit imposed by the configuration of the staple deforming die, acting in relationship with the anvil, during the said staple deforming die's full distance of travel.

Finally, it has been found to be necessary with conventional staples to provide more than one width to satisfy different wound situations, requiring the surgeon to stipulate beforehand the width he requires for a particular operation. Three widths are commonly used, designated 'normal', 'wide' and 'extra wide.' This necessitates duplication of staple manufacturing, assembly, identification stamping and packaging of the stapler devices, storing and recording by the manufacturer, as well as ordering and stocking by the end users i.e. hospitals, medical centers, and the like.

This invention is addressed to these drawbacks.

SUMMARY OF THE INVENTION

This invention provides a surgical stapling device comprising:
a body having a forward end,
a stapling station at the forward end,
a staple magazine in the body, arranged to feed the staples toward the stapling station,
an anvil and a reciprocable staple driver, or staple driving die both located at the stapling station, and
means for controlling the driving operation so that the preformed eliment is deformable to an initial closed position whereafter if desired further closure follows beyond such position for a purpose to be described later.

The body may be shaped like a pistol, for ease of manipulation. The body may therefore include a slim, box-like chamber portion for housing the mechanisms and a pistol grip portion, the junction between the grip and the chamber having a curved stop which is located opposite the curved trigger whereby the stop and trigger define a zone easily engageable by either the forefinger and thumb or the forefinger and thenar web.

The body may be made of a pair of left and right handed interfitting moldings.

The forward end may be about staple width in order to permit useful vision of the stapling site. The driver may be actuated by the pistol trigger.

The control may be achieved by an adjustable stop which stop as repositioned varies the distance of driver travel. Trigger and therefore staple drive die travel effects initial bending of the staple in the region of both shoulders which closes the staple to the initial closed shape. The further travel causes additional bending in the region of both shoulders tending to press or urge together the tissue which is contained between the 'elbow' regions of the staple on both sides of the incision. This extra movement is available to maximize opposition of the edges of the wound or incision and minimize eversion.

The anvil may be tiltable prior to or during the emplantation or insertion of the staples between a work position in which it underlies the foremost staple in the magazine and a release position in which it tilts in order to clear or release the inserted staple. The tilting motion may be supplied by the same motion which actuates the driver. The anvil may consist essentially of a plate with a staple receiving slot which faces the staple magazine in register with the leading staple in the magazine, the lower edge of the slot acting as the anvil lip over which the staple is deformed.

Additionally, a pair of forceps may be provided in advance of the stapling station which are operable by the same motion which actuates the driver. The forceps may be closed by the first pressure of the trigger so that when the pads of the forceps are placed astride the incision and the trigger is squeezed the initial trigger travel is utilized in forceps closing. The forceps consisting of a yoke and mutually inclined barbed pads may be detachable from the stapler to suit surgeons who prefer to use the stapler with separate standard forceps.

The trigger may have a return leaf spring which exerts first and second pressure by varying contact with internal body surface of the stapler which surrounds the spring. The trigger may be a molding made of a thermoplastic material with high flexural modulus so that the spring is integrally incorporated as a cantilever. Two separate protrusions may be molded into the hollow internal body casing of the stapler in order to sequentially obstruct the leaf spring during its travel and provide the said first pressure and second greater pressure. The driver and the anvil may be moldings suitably stiffened by pairs of ribs. Thus the whole stapler may be made of several moldings which permit economic manufacture and assembly of a disposable item.

The stapler of this invention therefore may comprise a body having a forward end, a magazine of staples in the body, arranged to feed the said staples toward the stapling station, an anvil and a reciprocable staple driving die both located at the stapling station, a pair of skin gripping pads mounted one on each side of the forward end of the body in advance of the stapling station, such pads being convergable to an inner stationary position the opposed edges of the incision, and means for actuating the die stagewise so as to permit staple insertion and closure to a first preselected position and thereafter further closure if needed to a second preselected position, the anvil being tiltable between a working position in which it underlies the foremost staple and a release position in which it stands clear of the closed staple such tilting being actuated by the die actuating means, the arrangement being that the forceps closing, die operation and tilting occur in sequence.

The invention also includes the combination of a stapler having an anvil and a staple driver, or driving die a surgical staple for closing a wound or incision, such staple in its blank form (prior to reformation) having a concave back about equal in length to the anvil lip width, a linear upper arm portion extending tangentially from each end of the back which extends the concave shape of the back and a linear lower arm portion extending downwards or downwardly and slightly inwardly from each of the upper arm portions, and the staple after insertion or implantation having a hexagon like configuration with an open side spaced between the opposed sharpened points.

The driver is so constructed and so operated that it produces the desired sequence by progressive exertion of a cam action on the forceps in order to converge the skin gripping pads to an inner position.

A feature of the stapler of this invention is the provision of a staple as herein described, an anvil and a driver the driving action thereof, and the staple deformation geometry being such that the points of the staple each follow a substantially linear path into the skin or fascia of the patient.

Another feature of the invention is a stapler in with the parts of the stapler operate in sequence to mechanically approximate the opposing sides of the wound or incision preparatory to staple insertion, to insert the staple points perpendicular into the skin of fascia in complimentary linear paths to render adjustable the degree of closure of the staple and to release the staple from the stapler.

The corner edges of the driver which contact the staple may be radiused or faceted. These edges contact and depress the upper arm section of the staple. Thus, the flat leading edges of the driver do not contact the staple.

One embodiment of the invention will now be described with reference to the accompanying drawings in which:

FIG. 1 is a side sectional elevation of the stapler;

FIG. 2 is an end elevation of the stapler from the front;

FIG. 3 is an end elevation of the stapler from the rear;

FIG. 4 is an underneath plan;

FIG. 5 is a plan;

FIG. 19 illustrates an exploded perspective view of a staple magazine;

FIG. 20 illustrates a side elevation of the base of the apparatus of FIG. 19;

FIG. 21 illustrates a plan view of the base of the apparatus of FIG. 19;

FIG. 22 illustrates a sectional view through the center line of the apparatus of FIG. 21;

FIG. 23 illustrates an end elevation of the apparatus of FIG. 20 and also shows the apparatus of FIG. 24 in end elevation as seen in FIG. 27 chain dotted in the assembled position;

FIG. 24 illustrates a side elevation of the lid of the apparatus of FIG. 19;

FIG. 25 illustrates a plan view of the apparatus of FIG. 24.

FIG. 26 illustrates a sectional view through line VIII through the apparatus of FIG. 25;

FIG. 27 illustrates an end elevation of the apparatus of FIG. 24;

FIG. 28 illustrates a view along arrows X—X of the apparatus of FIG. 24 with a staple in position;

FIG. 29 illustrates a view along arrow XI of the apparatus of FIG. 24;

FIG. 30 illustrates a staple in the apparatus of FIGS. 19 to 29;

FIG. 31 is a sectioned and elevation through XII; and

DESCRIPTION OF THE PREFERRED EMBODIMENT

Figure 1A:
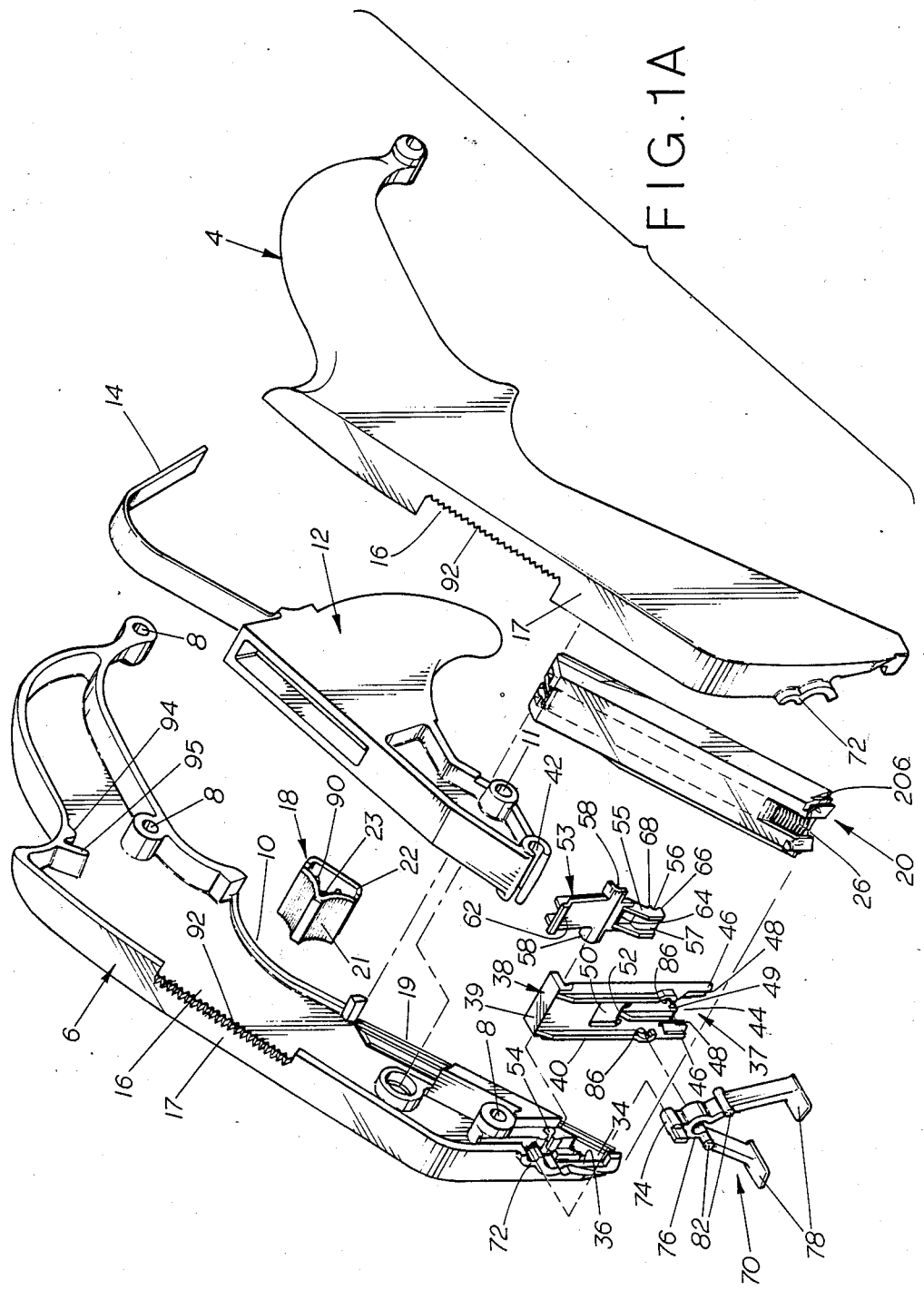
FIG. 1A is an exploded view of the stapler of this invention.

Referring now to the drawings and in particular FIGS. 1 and 1A, a stapling gun 1 comprises a body 2 which is made from two pistol shaped interfitting moldings 4, 6, which are a push fit on three location connection pins 8 and are sealed together by ultrasonic welding. The moldings have an underside slot 10 through which a molded trigger 12 protrudes. The trigger is mounted on pin 11 and trigger pressure is provided by cantilevered leaf spring 14. A slot 16 in the top of the body allows a button 18 to protrude for a purpose to be described later.

Figure 7:
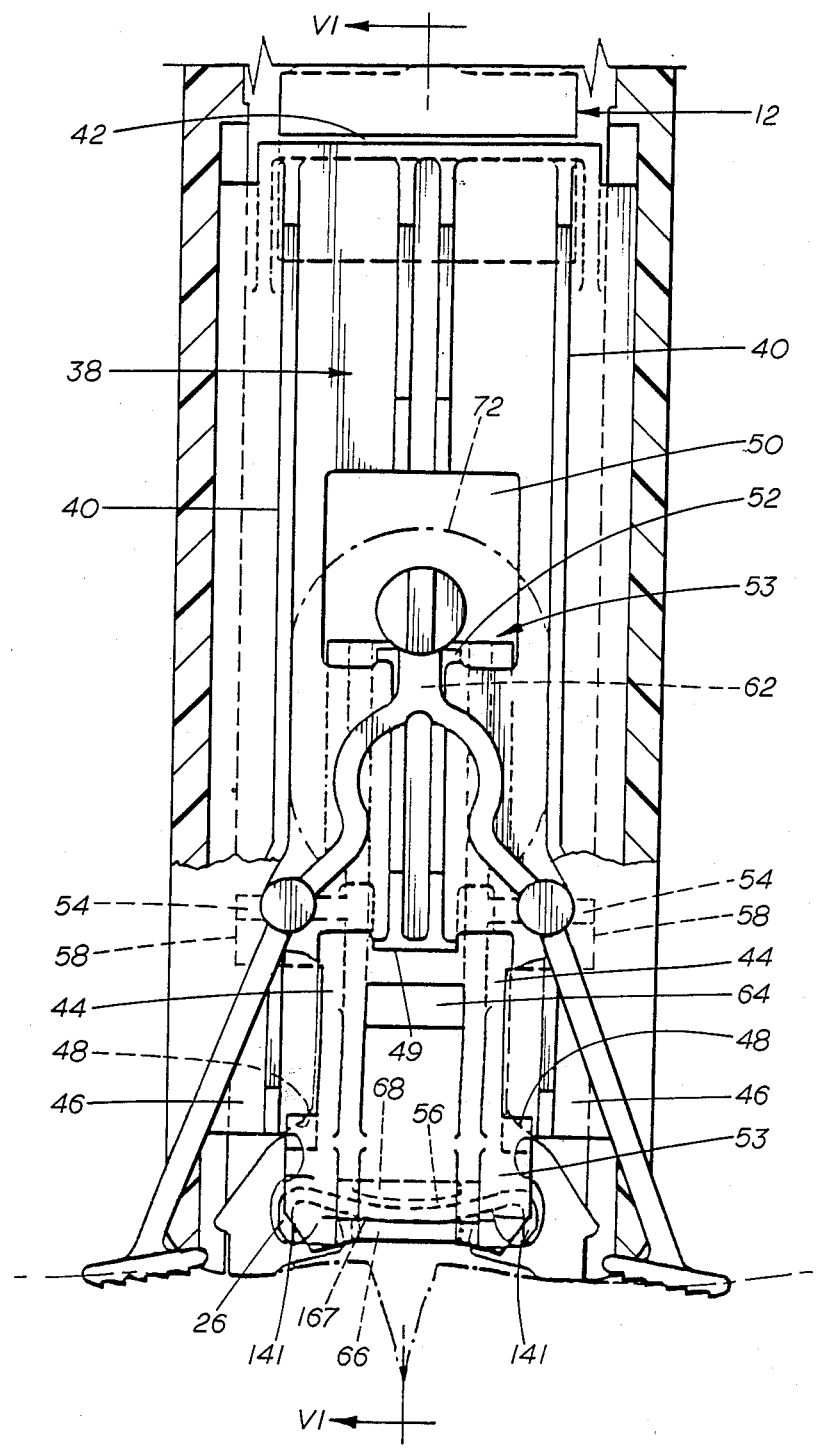
FIG. 7 is a front elevation of the parts shown in FIG. 6.

The forward end of the body moldings 4 and 6 have parallel slots 36. The molded driver or staple driving die 38 strengthened by ribs 40 rides up and down in the slots 36. The upper end of the driver 38 has a tab 39 which projects into a notch or socket 42 in the end of the trigger molding 12. The lower end of the driver 38 (see FIGS. 7 and 9A) has a cut out 44 and downwardly projecting twin pushing means or pushers 46 on both sides of the cut out which are provided with cam faces 48 which make contact with the staple. A horizontal lower bearing edge or cam surface 49 is provided by the driver which has a central window 50 and an upper bearing edge 52 at the edge of the window for a purpose to be described next.

A notch 54 molded in both halves 4, 6 of the body moldings above staple station 34, serves to mount a tilting or pivoting anvil plate 53 with central mounts 58 which enter notches 54 in the body moldings 4 and 6. The said anvil plate has upper cam faces 62 which cooperate with upper bearing edges 52. Likewise the said anvil plate has lower cam faces 64 which cooperate with lower bearing edges 49 as the driver rises and falls. The lower most part of the anvil has a lip 66 around which the staple is reformed, a ridge 68 above the lip for containing the staple back 129 during reformation of said staple and a slot 56 between the lip and ridge for receiving and locating the said concave central back region of the staple prior to and during implantation.

Figure 6:
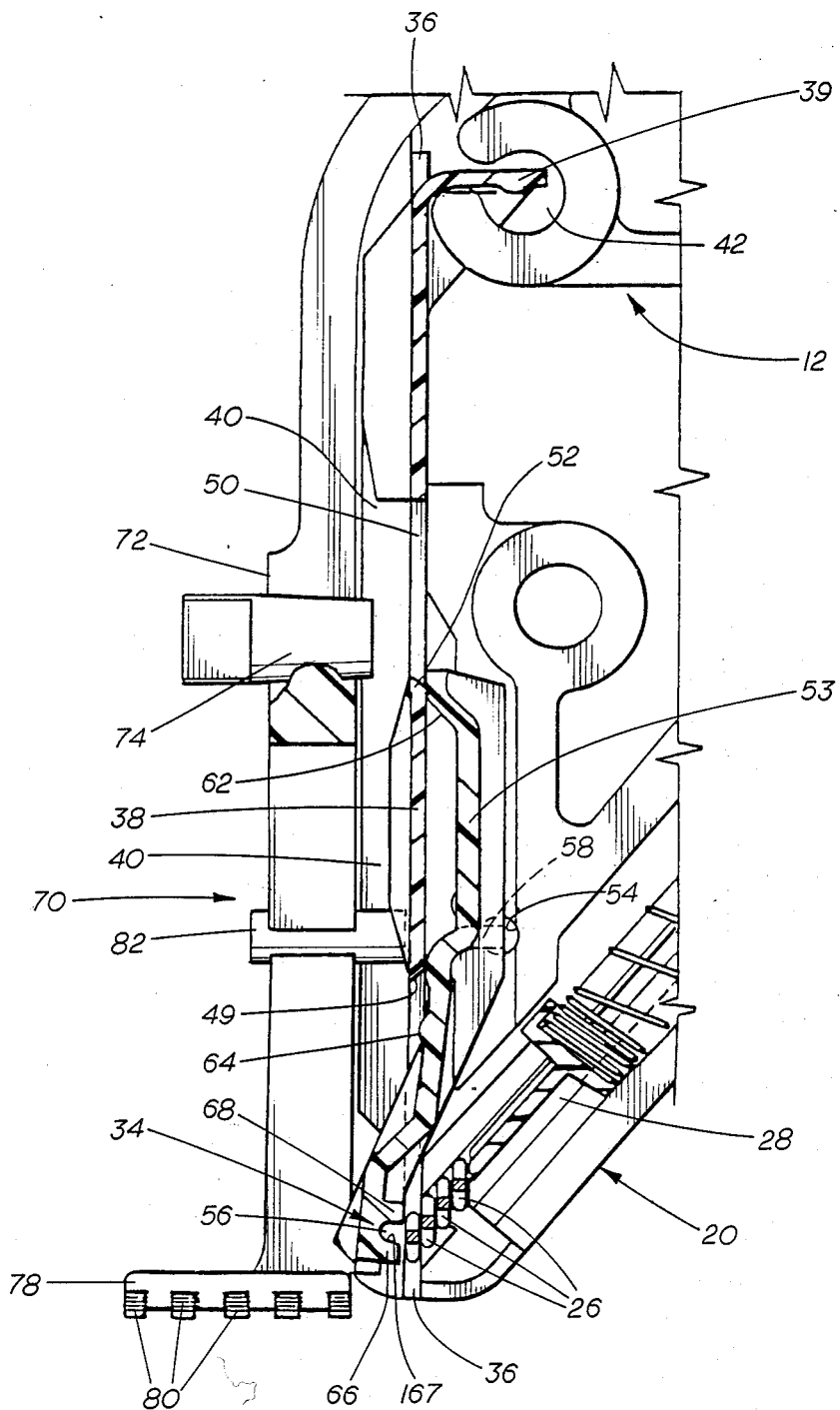
FIG. 6 is a fragmentary sectional elevation of the stapling station in the rest position.

From FIGS. 1, 1A and 6 it will be seen that trigger spring 14 biases the driver 38 to the raised position which causes upper bearing surfaces 52 to press the tilting anvil assembly to the position shown in FIG. 6. In this position the lip 66 rests clear of the foremost staple fed from the magazine. Conversely descent of the driver relocates the lip 66 beneath the foremost staple, the said staple being held in position in the work station gap 206 by the pimples 213 (as previously described in the description of the magazine and as illustrated in FIG. 28). The pushes 46 thereafter descend on both sides of the anvil bending the back of the staple (see FIGS. 6–15) progressively reforming the staple during implantation into the patient's skin or fascia.

Forceps Assembly

Figure 8:
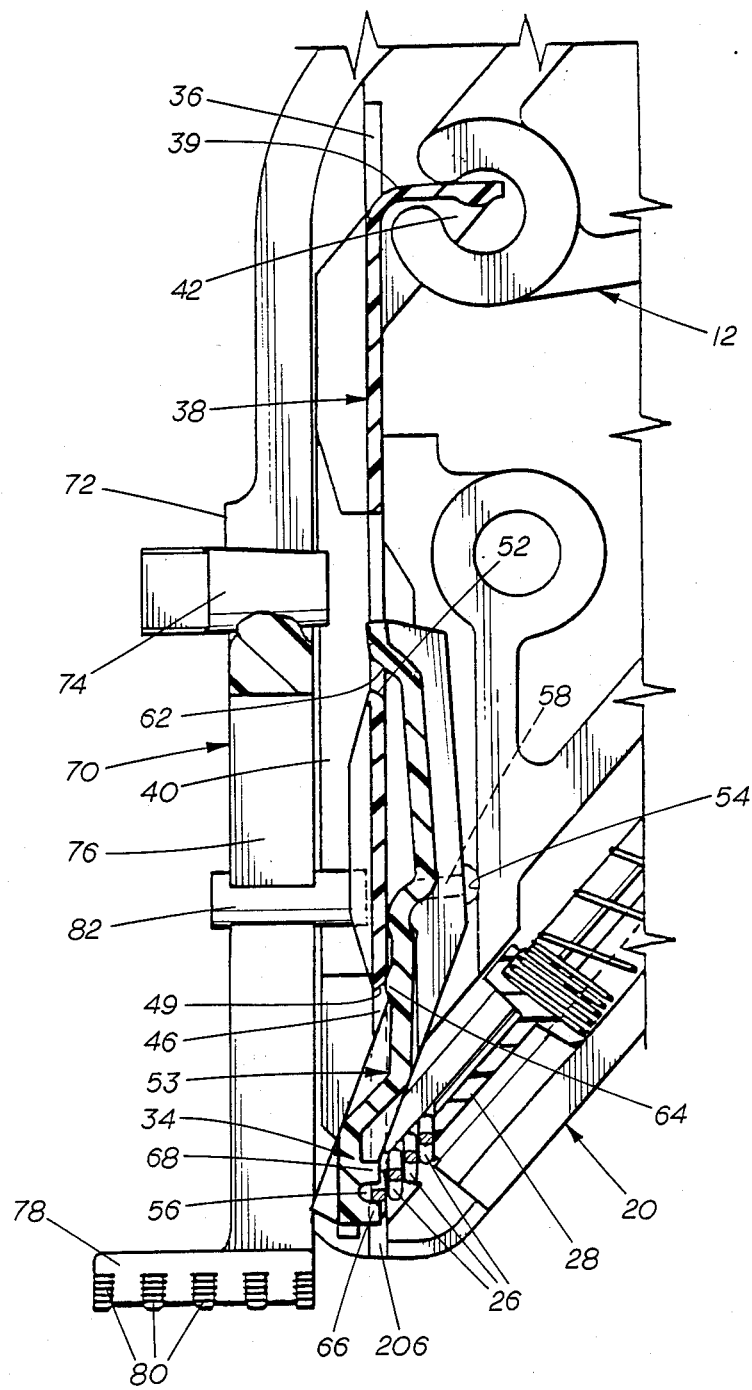
FIG. 8 is a fragmentary sectional elevation of the stapling station showing the anvil tilted to the stapling position in the initial stage of driver travel.
Figure 9:
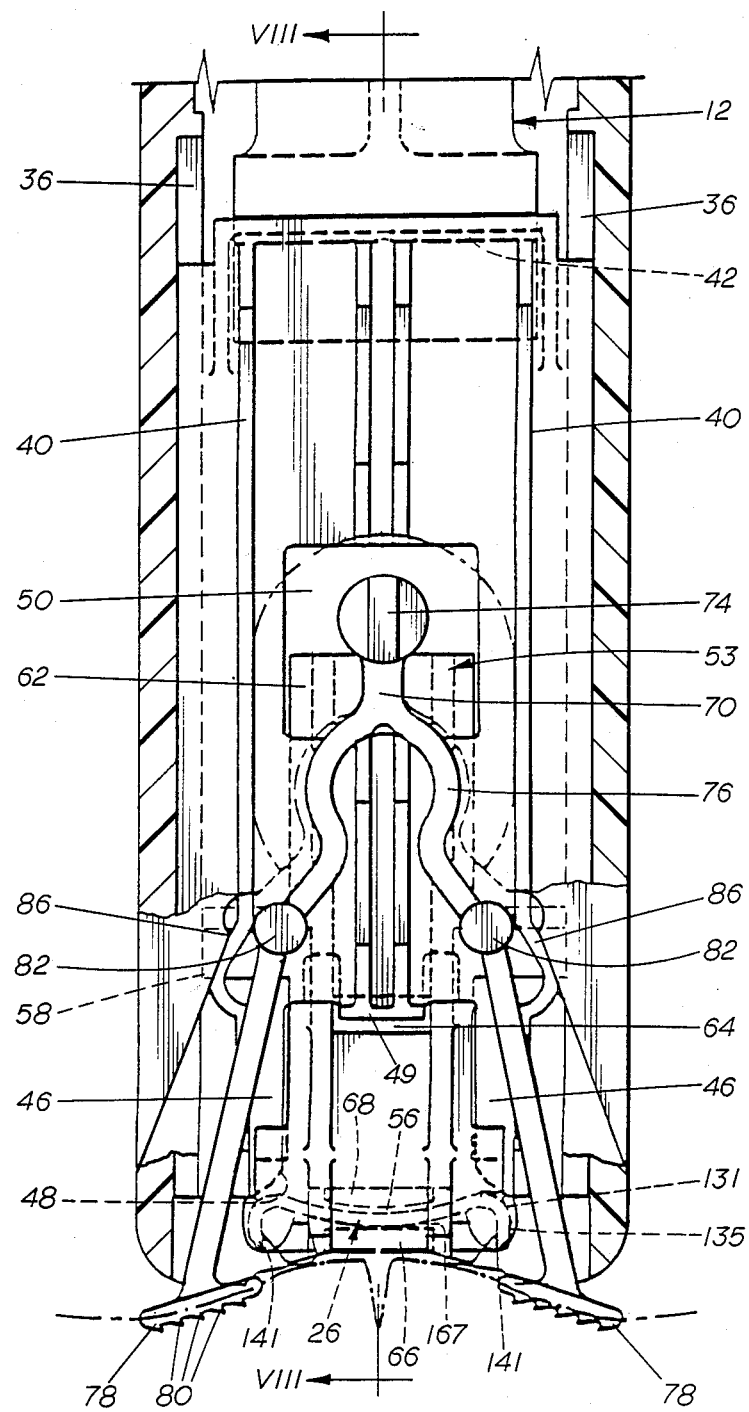
FIG. 9 is a front elevation of the parts shown in FIG. 8 also showing closure of the forcep pads during the initial stage of driver travel.
Figure 9A:
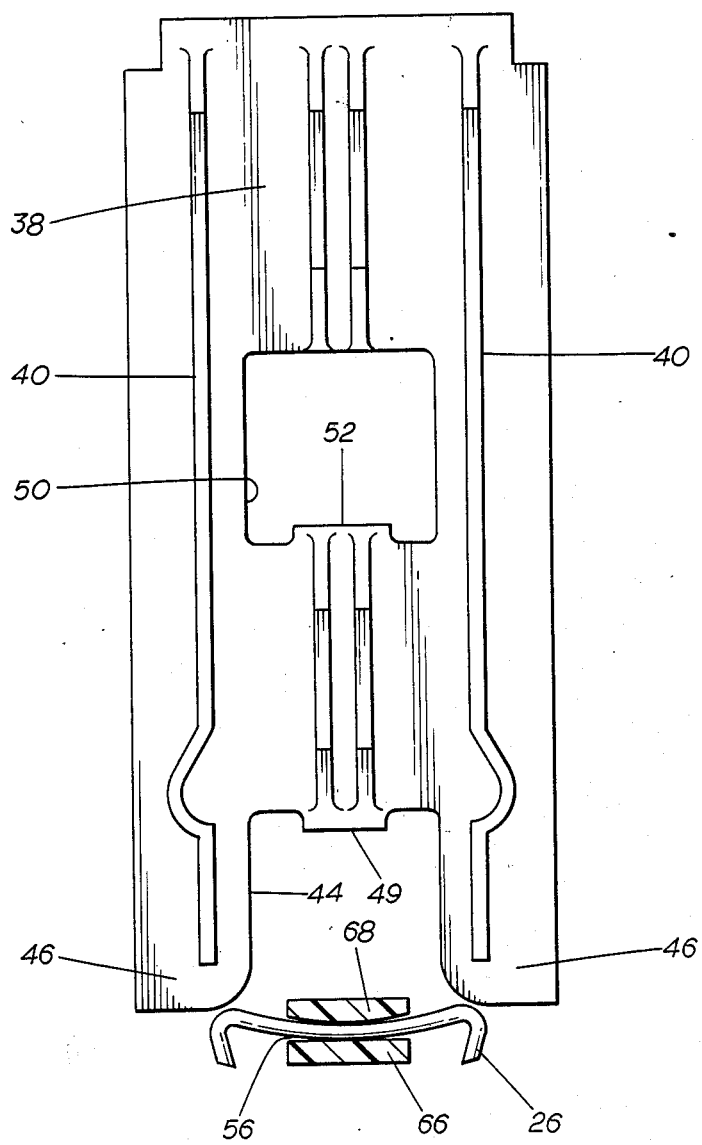
FIG. 9A is a front elevation of the driver die positioned to initiate bending of the staple held by the anvil.
Figure 10:
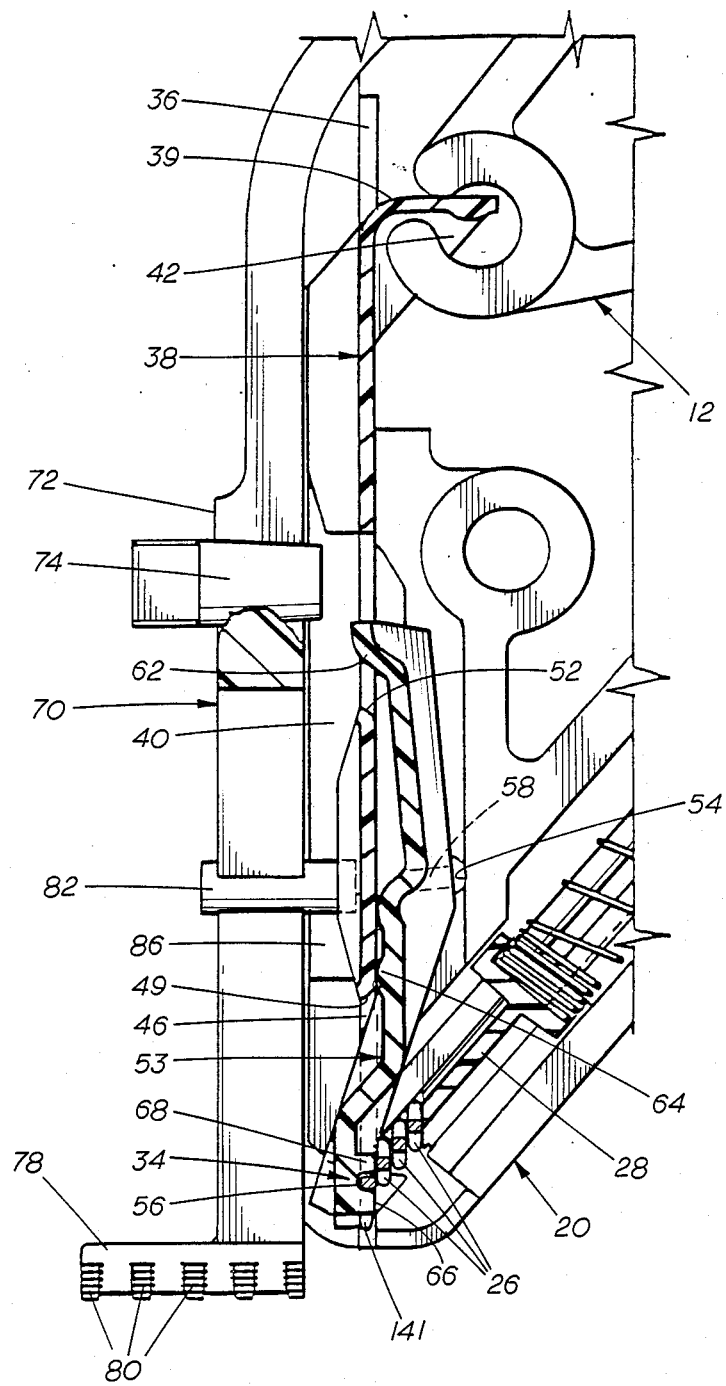
FIG. 10 is a fragmentary sectional elevation of the stapling station showing the onset of staple deformation to the point where concave staple back has been straightened.
Figure 11:
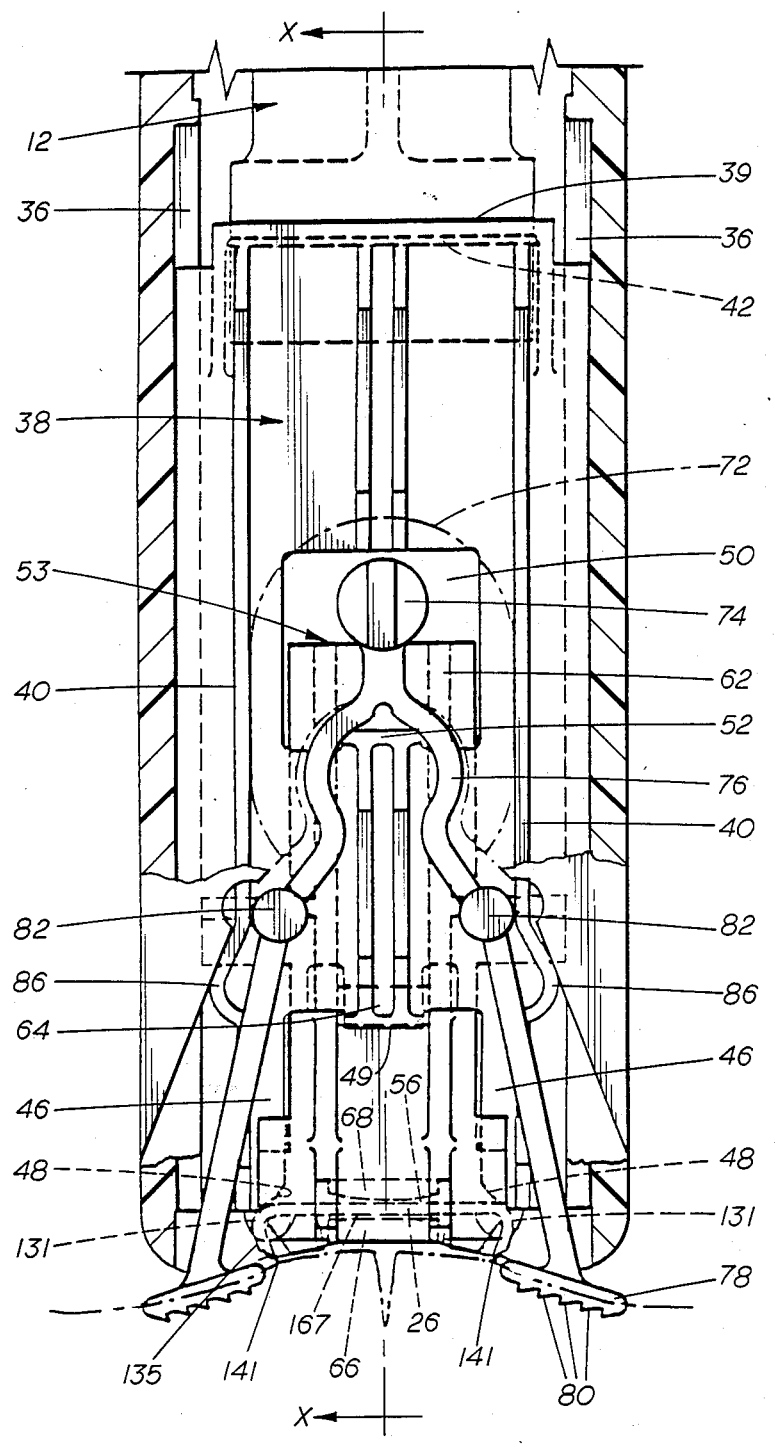
FIG. 11 is a front elevation of the parts shown in FIG. 10 showing the staple points in substantially perpendicular contact with the skin surfaces.
Figure 12:
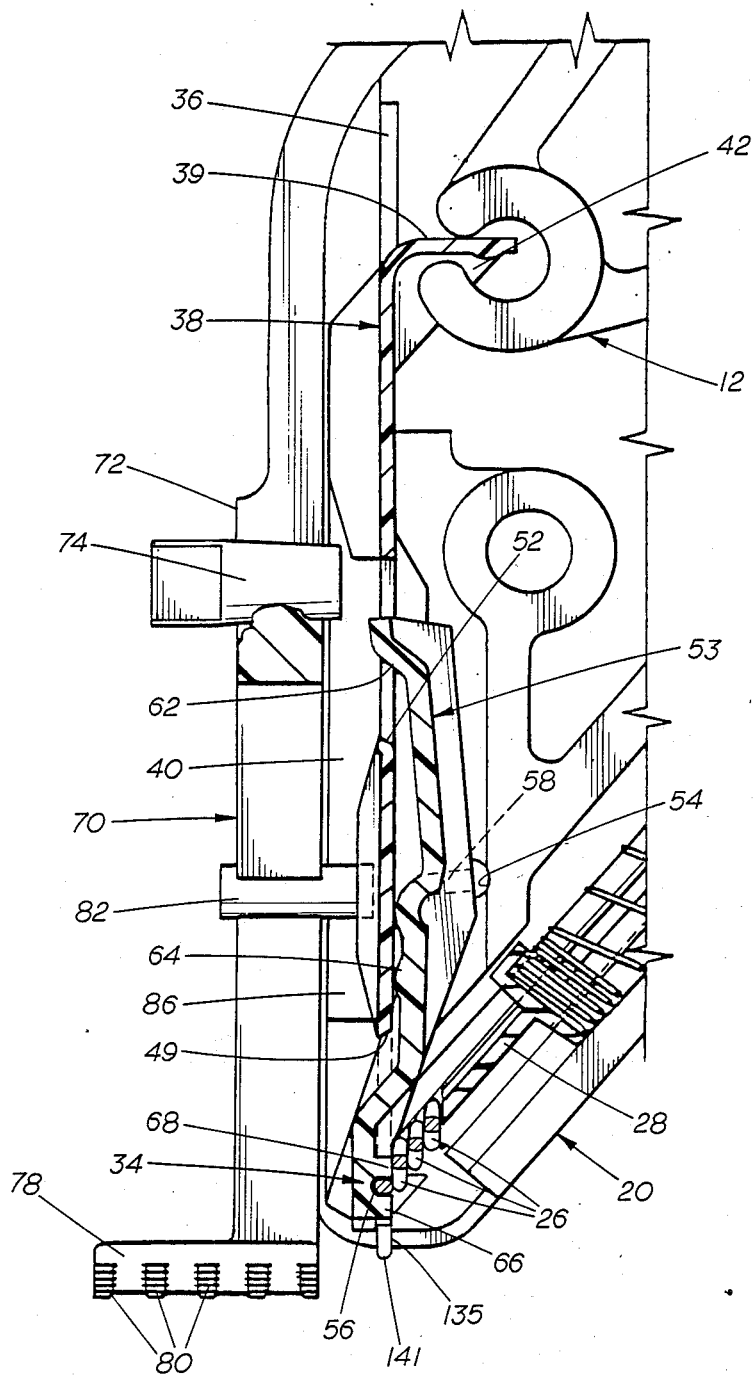
FIG. 12 is a fragmentary sectional elevation of the stapling station showing the inclusion of staple insertion to the initial closed position.
Figure 13:
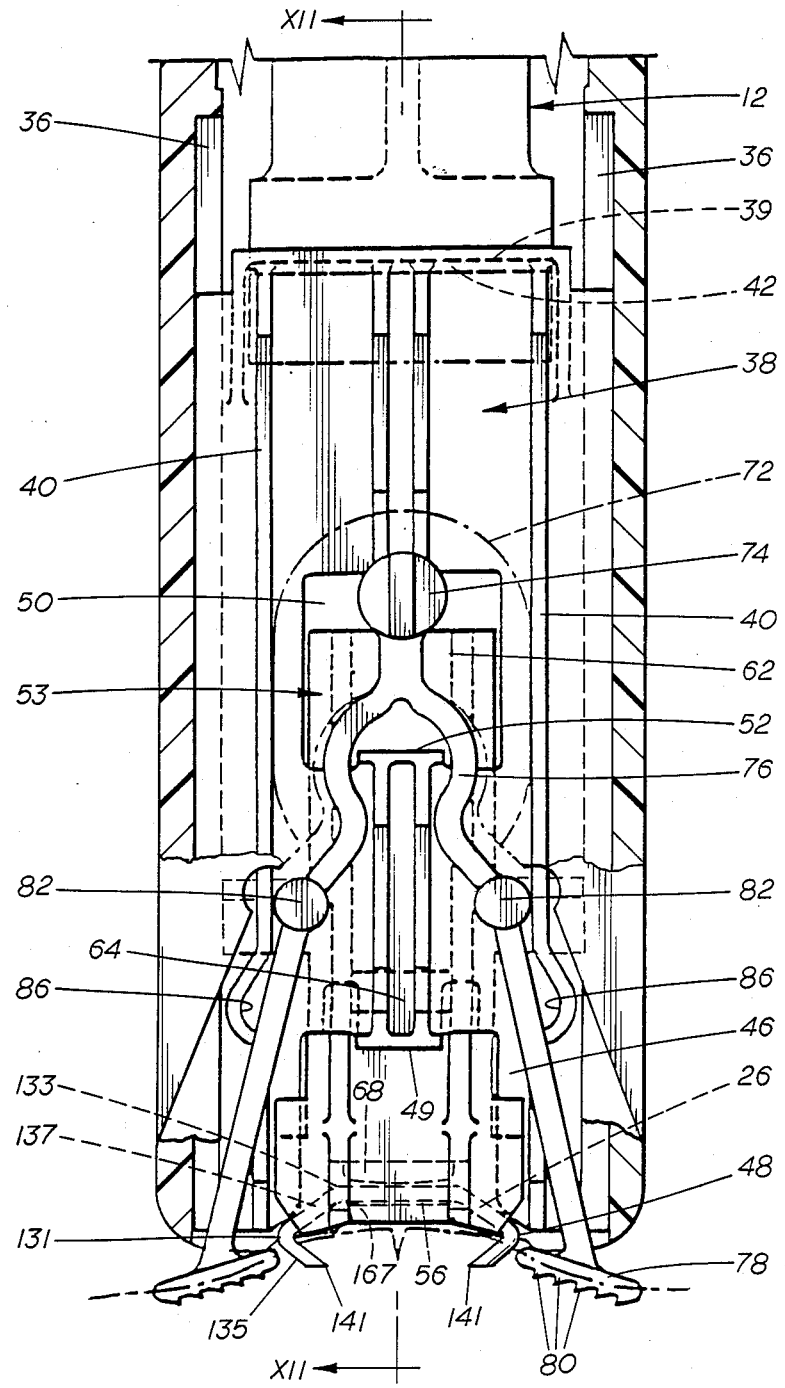
FIG. 13 is a front elevation of the parts shown in FIG. 12.
Figure 14:
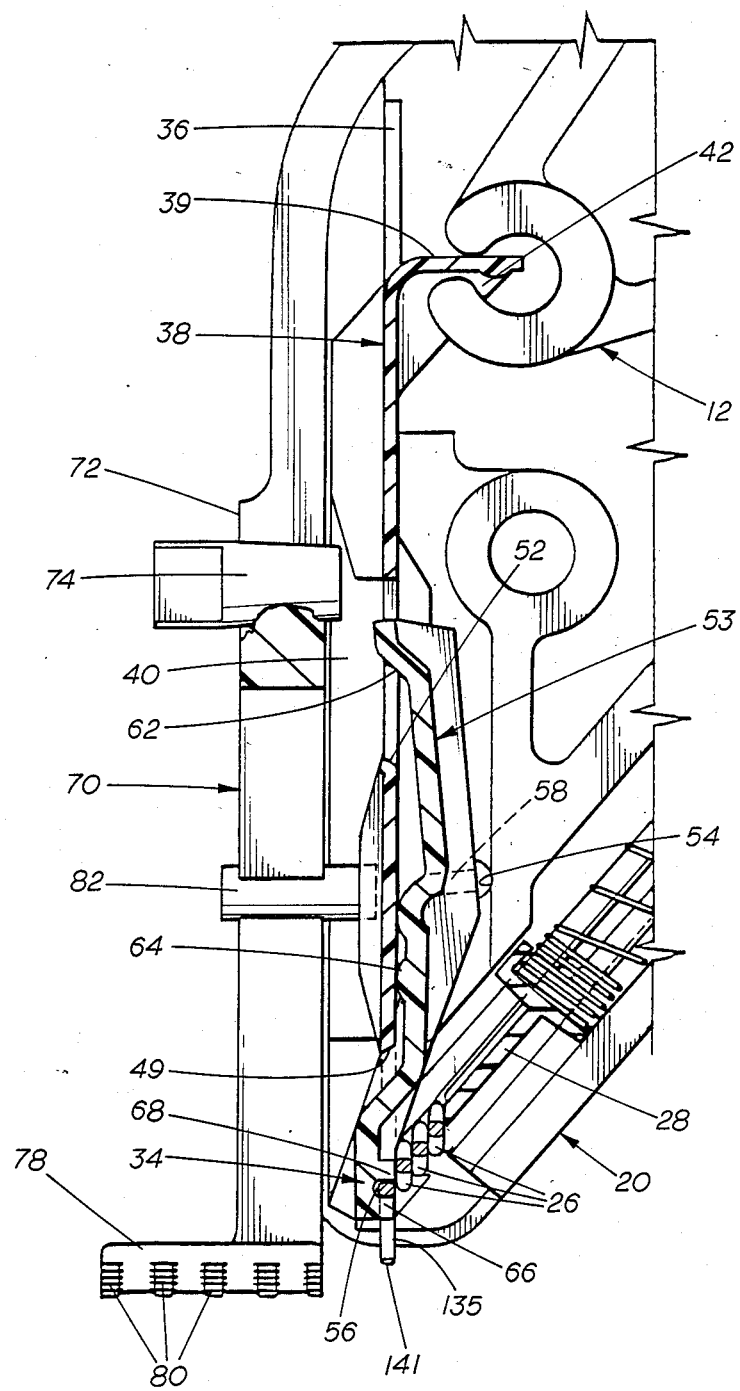
FIG. 14 is a fragmentary section of the stapling station showing the staple in its final closed position, with the stop at maximum and the trigger fully depressed.
Figure 15:
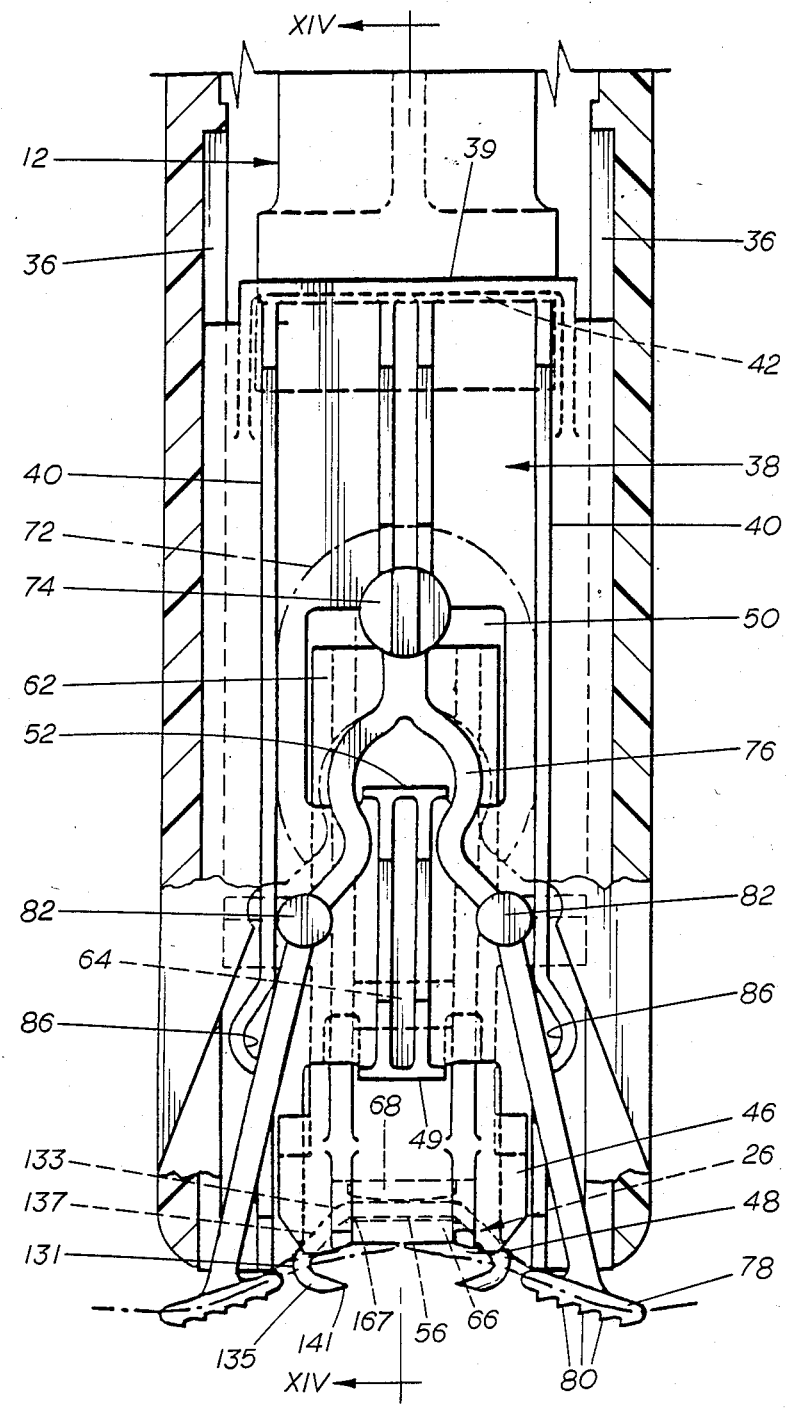
FIG. 15 is a front elevation of parts shown in FIG. 13.

Referring now to FIGS. 8 and 9, the nose 72 of the stapler mounts a forceps assembly 70 via a tapered pin 74. The assembly consists of yoke 76 the upper end of which is carried by the pin 74 the lower or opposite ends of which terminate in pads 78 which have rows of teeth 80 for gripping the patient's skin. Each of the leg members has a pin or knees 82 which project toward the driver 38. The driver also operates the forceps by means of a pair of mutually parallel ribs 40 which have cam profiles 86 allowing maximum separation of pads 78 when the driver is at its highest point or rest position but causing the pads to converge to reposed inner or stationary inner position during initial descent of the driver.

Button 18 has a pad 22 which contacts the trigger molding 12 which limits the trigger travel to prevent inadvertent over-adjustment of the staple between the initial and final closed positions of the staple. Button 18 has a toothed or separated stem 90 which reacts against the toothed edge 92 of slot 16 to give click stop positions.

When the trigger 12 is squeezed first pressure is encountered by leaf spring 14 pressing against the inside of pistol grip part of the body casing 2, second pressure is encountered when leaf spring 14 encounters nib 94 by virtue of shortening its effective length. This coincides with the driver cam faces 48 making contact with the elbow regions of the staple. A third and highest pressure is encountered when the leaf spring 14 encounters the further nib 95, thus further shortening its effective length. This coincides with the reformation of the staple to the initial closed position and this highest pressure remains during the adjustment sequence to the final closed position of the staple.

Bow Spring Retractor

In our U.S. Pat. No. 4,753,237, we have described a bow spring retractor for exerting a closing force on an incision and it is intended that the stapler of this invention may be used with that bow (see FIG. 32). When the bow is in position and the edges of the incision have been drawn into approximate apposition, the pads 78 are placed on the patient's skin straddling the incision.

Magazine

As illustrated in FIGS. 19 to 29, a magazine 20 is loaded into the underside of a stapling gun 1 (see FIG. 1) where it fits into the cavity 19 in snap-in engagement. The magazine 20 is comprised of a top member 201 and a bottom member 202, both of which are molded from transparent plastic material, and an end plug 203 which will be described later.

The top member 201 is positioned and joined with the bottom member 202, preferably by ultrasonic welding. An integral pair of tabs 204, located at the forward end of the top member 201, is attached to, but spaced apart from the top member 201 by a pair of short integral webs 205 which form a gap 206 with the front surface 207 of the forward end of the bottom member 202. The gap 206 is approximately equal in width to the stapler wire diameter and becomes an integral portion of the stapling station 34 when the magazine 20 is fitted in the cavity 19 of the body of the stapling gun 1. The tabs 204 and the front surface 207 of the bottom member 202 form restraining surfaces to prevent each staple 26 from rotating in the natural line of least resistance during bending and implantation of the staple 26. The tabs 204 and front surface 207 are inclined at an acute angle in relation to the longitudinal plane of the assembled magazine 20 when viewed in side elevation. The angle of inclination is equivalent to the angle which is formed between the longitudinal axis of the magazine cavity 19 in the stapling gun 1 and the driving die guide slots 36.

The staples 26 are loaded into the magazine 20 from a rearward end 208 of the magazine 20 and are transported forward in an aperture 209 which is formed by the shapes of the internal surfaces of the joined top member 201 and bottom member 202 respectively. The shape of the aperture 209 is such that is accurately locates and enables the feeding of a row of aligned staples 26 through it.

Alignment is accomplished by close tolerancing on surfaces with which the staples 26 are in contact and which serve to control and guide the staples 26 as mentioned previously. By the further feature of laying the staples 26 back at an angle in the aperture 209, such inclination of the staples 26 when viewed in end elevation is approximately parallel with the staple station gap 206. In this attitude, the sharpened points 141 of the staple 26 are prevented from contacting the surfaces of the aperture 209 while they are being transported forward in the magazine 20.

In order to accurately incline the staples 26 forward in the aperture 209, two longitudinal parallel guide rails 220 are molded on the inner surface of the bottom member 202 so as to support the staples 26 on the undersides of their upper arm regions 137 outwardly of the points at which the upper arm regions 137 tangentially connect with the curved back regions 129 on the staples 26. The support of the guide rails 220 is thus directed to the underside of the upper arm regions 137A slightly above the midpoint of total elevation between the lowermost portion of the curved back region 129A and the uppermost portion of the inner curve of the elbow region 131A of the staple 26, when viewed in side elevation with the guide rail support 220 being also substantially in line with the center of mass of the staples 26.

It can now be seen that when a load is applied downwards upon the upper surfaces of the two elbow regions 131 of the staples 26, as indicated by arrow 300 on FIGS. 30 and 31 the staple 26 can be caused to rotate either clockwise or counter-clockwise around a fulcrum or pivot point when viewed in end elevation (FIG. 31), the fulcrum being constituted by points of contact between the guide rails 220 and the undersides of the upper arm regions 137A of the staples 26. It can thus be appreciated that the sharpened points 141 of the staples 26 can be rotated in a pendulum fashion, away from the base surface 226 of the channels 219, a sufficient distance to prevent them making contact with the base surface 226. When the angle of rotation of the staple 26 exceeds approximately 25 degrees from the vertical plane in either a clockwise or counter-clockwise direction, it becomes progressively counterbalanced by the multiplying effects of the projected extension of the staples; center of mass about its moment arm, tending to counter-rotate the staple 26 to an upright attitude. By providing the downwards load to the upper surfaces of the two elbow regions 131 of the staples 26 (in the form of fixed surfaces 221 formed on the internal surface of the top member 201) the fixed surfaces 221 being elevated in the aperture 209 above the guide rails 220 by a distance such that when the staples 26 are fed into the aperture 209 in a laid back attitude, the distance separating the fixed surfaces 221 from the guide rails 220 will cause the staples 26 to lie at an inclined angle in the aperture 209, approximately parallel with the angle of station staple gap 206 as described previously. In this position, the staples 26 are in equilibrium about their fulcrums or pivot points, balanced by the opposing downward moment of the fixed surfaces 221 and the projected center of mass of the staples 26. It will also be appreciated now that contacts between the staples 26 and the aperture 209, are in fact point contacts and as such these contacts exert very little frictional resistance.

To control the final phase of alignment of the staples 26, which is to prevent transverse movement in relation to one another, (which if allowed could also result in staples slewing diagonally across the guide rails 220) close tolerance guide edges 222 are provided, running longitudinally in the aperture 209 so as to bear or almost bear against the inner surfaces of the lower arm regions 135 of the staples 26 of alternatively against the outer surfaces of the lower arm regions 135 substantially in the region of elbows 131 of the staples 26.

As each staple 26, in turn, reaches the staple station gap 206 at the forward end of the magazine 20, it is already aligned with the inclination of the gap 206 and will drop into it without hinderance until arrested by two pimples 213 molded on the inner surfaces of the tabs 204, there being one on each tab. The pimples 213 locate under the elbow regions 131 of the staple 26 and accurately position the said staple symmetrically in the staple station gap 206 and at the correct elevation within the said gap to ensure registration with the pivoting anvil 53 when the said anvil is tilted into its work position by the descending driving die 38. The protrusion of the pimples 213 into the work station gap 206 is such that they prevent the staple passing through the said staple station gap until forced through by the driver die 38 during bending of the upper arm regions 137 and subsequent implantation of the sharpened points 141 and lower arm regions 135 of the staples 26 into a patient. In order to force past the pimples 213 in the station staple gap 206, when acted upon by the driving die 38, the upper arm regions 137 of the staples 26 cause the tabs 204 to flex outwardly sufficiently to allow the wire diameter of the staple 26 to squeeze between the apex of the pimples 213 and surface 207 of the forward end of the bottom member 202 in the formed staple station gap 206. When the staple 26 is fed forward into the staple station gap 206 and is arrested by the pimples 213, its elevation is marginally lower than the elevation of the remaining staples still within the aperture 209, but not sufficiently so that the next leading staple in the row still within the aperture 209 is able to feed forward over the top of the first staple in the staple station gap 206.

During implatation of the first staple into a patient, twin pushers 46 on the driver die 38 occupy the space in the staple station gap 206 so that the next leading staple cannot be fed in from the aperture 209 into the said staple station gap until the driver 38 is fully retracted to its rest position after completion of the implantation of the first staple. This sequence prevents the staples from jamming in the staple station gap 206. The staples in the aperture 209 are urged forward towards the staple station gap 206 at the forward end of the magazine 20 by a spring means 32 acting upon a follower 28 which bears against the rearward side of the last staple in the row. The follower 28 is sloped at its forward ends 216 so that the feeding force exerted by the spring means 32 is evenly transmitted to the row of staples 26 and does not tend to upset their angle of inclination. The complete assembly, comprising the row of staples, follower 28 and spring means 32 are locked into the aperture 209 by the end plug 203 mentioned previously. The plug 203 snaps into position in the rearward end 208 of the magazine 20 and is held in interference fit between two ribs 224 positioned one on each side of the plug, in corresponding indentations 225 molded into the rearward ends of the top and bottom members 201 and 202 respectively.

When viewed in end elevation, the configuration of the magazine 20 is such that it shows a radius nosed linear flange 217 running longitudinally along the midsection of each side of the magazine 20, beginning adjacent the forward end of the magazine 20 and tapering out onto flat surfaces 218 beginning about two-thirds of the length of the magazine 20 towards the rearward end 208. The flanges 217 and tapered flats 218 enable the magazine 20 to be positively located and snap fitted into the cavity 19 of the stapler 1.

Another version of the magazine is the subject of U.S. patent application Ser. No. 061893.

After sterilizing, the instrument is ready for use and after using same, it is disposed of.

Operation

The sequence of operations when this trigger is squeezed is as follows:

Total trigger travel when squeezed, causes a progression of reactions to the various mechanisms within the stapling tool, culminating in a staple being forceably implanted into the patient's skin and underlying tissue, and adjusted to close the wound to the surgeon's satisfaction. The following is a description in sequential order of this progression.

1. The primary portion of trigger travel is utilized in squeezing in the patient pins 80 of the forceps yoke 76 in order to reposition the pads 78 inwardly to their innermost position.

2. The secondary portion of trigger travel is utilized in fully pivoting the anvil plate rearwardly to its operating position, where it registers with and restrains the leading staple in the work station gap 206. Pivoting the anvil plate is accomplished by means of a cam reaction between it and the downward linear motion of the driving die 38, as described in the foregoing text.

Figure 16:
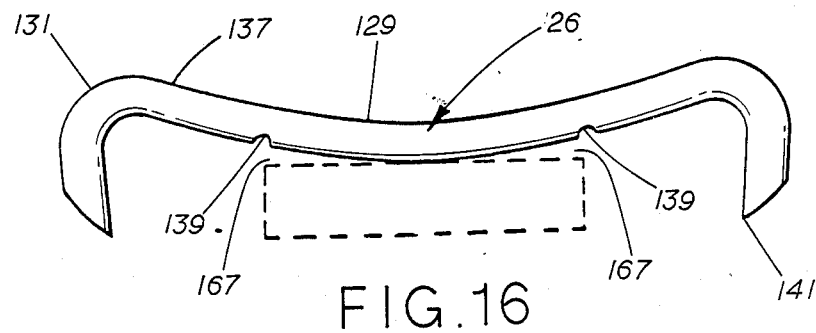
FIG. 16 is an elevational view of staple or preferred staple element before commencement of deformation.
Figure 17:
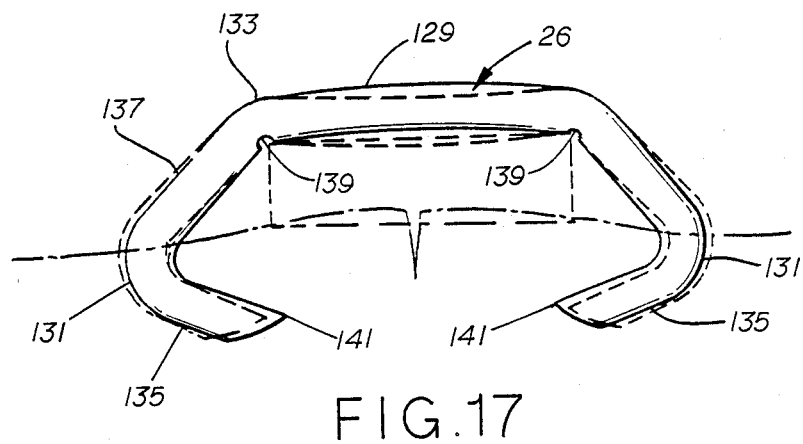
FIG. 17 is an elevational view of staple in the final closed position after release from the stapler with ghosted lines indicating the amount of spring back.

3. The tertiary portion of trigger travel is utilized in forming and implanting the staple into the patient's skin. This is achieved by bending the staple, its back region now restrained in the slot 56 of the anvil, over the lip 66, said lip being located on the bottom most extremity of the anvil plate 55, by the continued downward motion of the driver 38. Said driver is formed with a downward pointing finger or pusher 46 on each side extremity, said fingers or pushers being so shaped on their innermost edges 48 so as to engage with the staple and cause controlled downwards reformation of the upraised 'elbow' regions 131 of the staple, causing bending of the 'back' region 129 of said staple about the edges 167 of anvil lip, (see FIG. 16) thus forming 'shoulder' regions 133 in said staple and causing 'pointed ends' 141 of 'lower arms' 135 extending from said 'elbow' region of staple to be forceably inserted into the patient's skin. The regions of the staple between the 'shoulder' 133 and 'elbow' 131 are referred to as the 'upper arm' regions 137. Pre-crimping or chatching 139 of the staple immediately beneath the 'shoulder' regions helps to control bending and minimizes 'spring back.'

4. A modified portion of tertiary trigger travel is also provided. This is utilized by adjusting the linear position of the moveable stop component 18 located in the top face 17 of the stapling tool. Rearwards travel of the stop component subsequently allows further travel in the trigger mechanism and consequently further travel of the staple driving die. Such additional travel is made against the third and highest trigger pressure as previously described. The amount of such trigger travel is governed by the precise respositioning of the stop component 18. Should the surgeon desire to use this adjustment provision to minimize the degree of wound eversion at the skin surface, it is suggested that the stop be adjusted in increments and the amount of free trigger travel resulting, be taken up. The degree of eversion can then be re-examined and reassessed, with further adjustment made if desired. In this way the surgeon will avoid inadvertently over adjusting. It can be appreciated that a substantial linear movement of the stop component 18 results in a substantially small amount of driver travel. Therefore very fine adjustment is provided. It should also be understood that for any surgeon familiar with the use of the stapler, (which is partially the subject of this invention) once the stop component 18 is set to correctly adjust the first staple, no further adjustment should be necessary to insert all subsequent staples to achieve uniform would closure and surface eversion.

With reference to paragaph 1 above, it should be understood that the orientation of the forceps pads 78 in relation to the yoke legs (see FIG. 7) and the geometry of the yoke leg movement ensure that the wound is fully apposed from its full depth with slight eversion towards and substantially at the skin's surface, thereby avoiding inversion. The skin and underlying tissue are in addition, caused to slightly 'mound up' (see FIG. 9) by the action of the forceps mechanism and the downwards pressure applied. Should the surgeon decide that the degree of mounding created by the full movement or travel of forceps mechanism is excessive, reduction of the downwards pressure exerted by thes surgeon via the stapling tool to the forceps pads 78 will allow the skin to slip outwardly away until the desired degree of mounding is achieved. At this point, increased downwards pressure to the forceps pads will arrest and prevent any further skin slippage and loss of mounding.

An alternative technique is to take up the initial forceps travel by commencing to squeeze the trigger of the tool, prior to placing the forceps pads in contact with the skin.

Factors which will affect the degree of 'mounding' resulting from the action of the forceps mechanism are:

(a) the degree of downwards pressure exerted by the surgeon via the stapling tool, into the forceps pads, (b) the elasticity or otherwise of the patient's anatomy in the region of the wound, and (c) the amount of sub-layer fat tissue below the region of the wound.

It is anticipated that even surgeons of slow adaptability will quickly learn to make compensation according to the nature of each wound, to produce a mound of the desired shape during the action of the forceps mechanism.

In reference to paragaph 2 above, it should be noted that the final portions of travel of the forceps pads 78 occurs during pivoting of the anvil plate 53 towards its operating position and that the limit of travel of the said forceps pads is reached to prior to the tips 141 of the 'pointed ends' of the staple—as a result of bending the staple 'back' over the anvil lip—coming into contact with the patient's skin. Thereafter, the forceps mechanism simply serves to retain the skin and underlying tissue on either side of the incision or wound in their pre-arranged mounded relationship to each other, while the staple is inserted and, if necessary adjusted.

Figure 18:
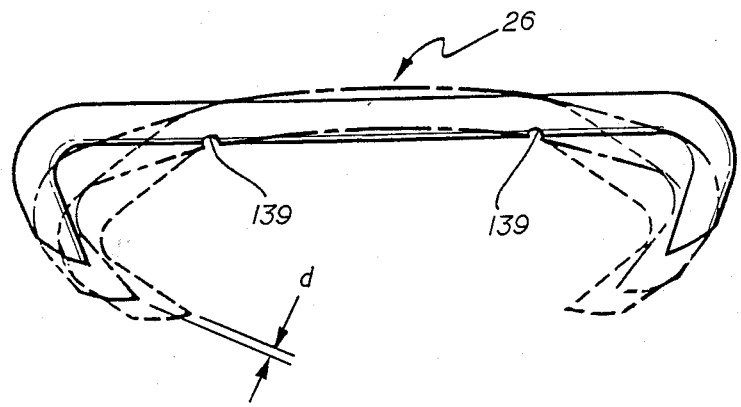
FIG. 18 is an elevational view illustrating the substantially linear path followed by staple points in penetrating the skin and underlying tissue to the depth of the elbow region, corresponding with the initial closed position.

In reference to paragraph 3 above, it should be understood that the 'pointed ends' 141 and 'lower arms' 135 of the staple penetrate into the skin and underlying tissue on opposing sides of the wound, each substantially in a linear motion, in a downwards and inwardly converging direction, until the approximate midpoint of the inner radius of curvature of the 'elbow' region 131 of the staple submerges to skin surface (epidermis) level. The slight deviation from a linear path during implantation is identified as the distance 'd' in FIG. 18. This degree or depth of penetration of the 'pointed ends' of the staple is designed to occur substantially at the limit of the initial tertiary stage trigger travel. It will be appreciated that hereafter, no appreciable additional penetration of the 'pointed ends' of the staple can occur even during the adjustment sequence, owing to the natural resistance resulting from the reverse angle of the 'upper arm' regions 137 of the staple leading from the radius of curvature at the 'elbow' region 131 of the staple towards the 'shoulder' region 133.

In relation to paragraph 4 above, it can be seen from FIG. 1 that the limit of trigger travel is governed by contact between the cam 22 of the stop component 18 (located at the forward end of the slot 16 in the top face 17 of the tool) and the top surface of the trigger 12. Simultaneously, the integral trigger spring 14, near the union with the trigger's body, contacts nib 95 of the main body casing, thus when the stop component 18 is adjusted rearwards along the top face 17 of the tool to allow further trigger travel, a third and highest trigger pressure is encountered.

Hence, when the staple has been reformed and implanted into the patient's skin and in the judgment of the performing surgeon, the wound substantially at the skin's surface remains too everted, he may, by repositioning the adjustable stop component 18 and further squeezing the trigger 12, apply additional bending to the 'shoulder' regions 133 of the staple in order to minimize the degree of wound eversion to his satisfaction. This adjustment is the equivalent of drawing tighter the knot of a threaded suture for the same purpose.

It will be noted that if the adjustable stop 18 is used in small increments, it will prevent the inexperienced surgeon from inadvertently over tightening the wound closure.

Figure 32:
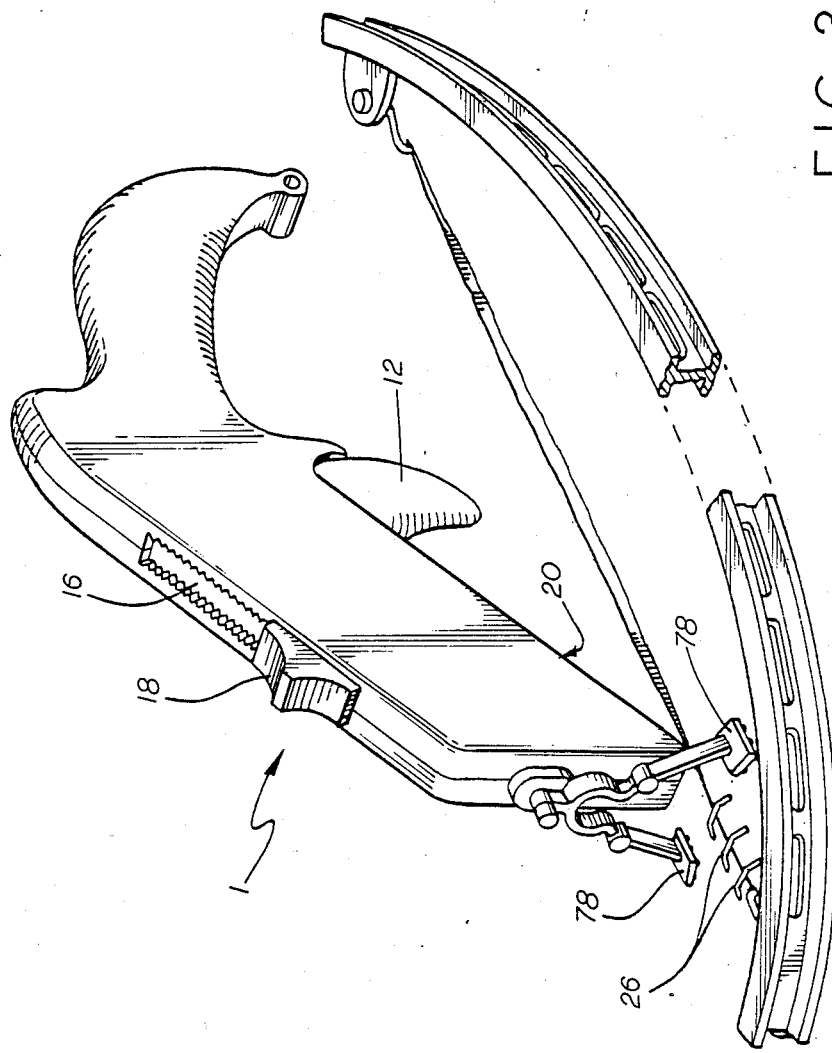
FIG. 32 illustrates the case of a stapling gun in accordance with this invention in co-operation with a retraction device.

It will be noted further that when used with any suitable method of uniform wound approximating and/or lifting, such as is provided by the bow spring retracting tool of FIG. 32, the position of the stop component 18 once set, should be correct for each subsequent staple needed to finish closing the wound.

Consequently, when the surgeon is satisfied that each staple 26 in turn has progressively closed the wound to a desirable degree (allowing for minimal 'spring back' by the wire staple) he releases the trigger 12, which is returned to its start or rest position by the stored up forces in the integral return spring 14. Thus, bending pressure exerted by the driver fingers 46 on the shoulder regions 133 of the staple is released as pusher 38 returns towards its start position. Next, the anvil plate 53 pivots forward releasing its constraining hold on the 'back' region 129 of the staple 26 thereby disassociating the said staple from the stapling tool. Finally, the reverse cam action and the stored up forces in the forceps yoke 76 causes the forceps mechanism to return to its rest position. The tool is now ready to be repositioned further along the wound or incision line to insert the next staple.

One further characteristic of this stapling system is that the mounding effect caused initially by the action of the forceps mechanism should ideally almost dissipate entirely as the skin and sub-layer settle back against the now constraining action of an inserted staple, after the forceps pads 78 are released from the skin. The resulting very slight residual mounding will ensure that the wound is now held nicely apposed and will not tend to invert. In this, it works in conjunction with the position and direction of the 'pointed ends' 141 and 'lower arms' 135 of the staple to keep opposing sides of the wound or incision in constant apposed relationship to each other, while never protruding so much that the least likelihood of permanent 'ridging' under the scar line may occur.

I have found the advantages of the embodiment described above include:

1. The forceps are detachable allowing the surgeon to use his own forceps if desired;
2. The forceps permit a degree of final manipulation of the edges of the incision depending upon the application or release from the pads;
3. The adjustable stop permits an initial adjustment to be selected which will draw the edges of the incision together exactly as desired by the surgeon whereafter the adjustment is preserved for subsequent staples;
4. Only one sample size is required for all closure procedures.

I claim:
1. Surgical staple element applicator, comprising:
a body adapted to be hand-held and having a forward end;
said body forming a stapling station at said forward end;
a staple-hold magazine mounted with said body for feeding a staple blank into position for reforming and implanting into the skin of a patient;
a staple driving die, said body having driving die mount means mounting said staple driving die for movement between raised and lowered positions, said driving die including pushing means for engaging and reforming said staple blank to a final substantially hexagonal configuration;
an anvil means for receiving a staple blank from said staple-holding magazine for engagement by said driving die pushing means;
said body including anvil mount means mounting said anvil means for movement between release and work positions;
a displaceable trigger assembly and trigger mount means mounting said displaceable trigger assembly with said body for pivotal movement, said displaceable trigger assembly being operably attached to said staple driving die for moving said staple driving die between said raised and lowered position in order to reform said staple blank into a substantially hexagonal configuration;

a forceps assembly mounted with said body, said forceps assembly including a pair of downwardly extending leg members connected to a resiliently flexible clevis;

at least one skin gripping pad located on each of said leg members; and said forceps assembly including cam engagement means for engaging complementary cam means on said driving die such that said pair of leg members and pads are converged to a stationary inner position in response to movement of said staple driving die from said raised toward said lowered position in order to selectively approximate the wound edges.

2. The forceps assembly of claim 1, further including:

said resiliently flexible clevis of said forceps assembly having means for detachably mounting said forceps assembly to said body.

3. The structure set forth in claim 1, including:

each of said leg members of said forceps assembly having a cam engaging element extending into engagement with a forceps camming surface located on said staple driving die, said forceps camming surface on said staple driving die moving each of said forceps leg members inwardly with respect to each other in response to movement of said staple driving die from said raised toward said lowered position in order to cause said skin gripping pads of said forceps assembly to engage and move said wound edges into selective approximation in preparation for implantation of a staple element.

4. The structure set forth in claim 3, including:

said forceps camming surfaces on said staple driving die including ridge portions on said staple driving die for engaging said cam engaging elements on said forceps leg members in order to converge said forceps leg members in response to movement of said staple driving die from said raised towards said lowered positions.

5. Surgical staple element applicator, comprising:

a body adapted to be hand-held and having a forward end;

said body forming a stapling station at said forward end;

a staple-holding magazine mounted with said body for feeding a staple blank into position for reforming and implanting into the skin of a patent and having at least one staple blank therein, said staple blank having a generally shallow concave configuration;

a staple driving die, said body having driving die mount means mounting said staple driving die for movement between raised and lowered positions, said driving die including pushing means for engaging and reforming said staple blank to a final substantially hexagonal configuration;

an anvil means for receiving a staple blank from said staple-holding magazine for engagement by said driving die pushing means;

said body including anvil mount means mounting said anvil means for movement between release and work positions;

a displaceable trigger assembly and trigger mount means mounting said displaceable trigger assembly with said body for pivotal movement, said displaceable trigger assembly being operably attached to said staple driving die for moving said staple driving die between said raised and lowered position in order to provide means to reform said staple blank;

said staple blank having an initial configuration in said staple holding magazine which includes a back portion which is substantially concave in configuration, said back portion includes a central concave portion having a linear upper arm portion extending tangentially upwardly and outwardly from each end of said control concave portion, which extends the concave configuration throughout the width of said back portion;

a tightly curved elbow portion extending downwardly from the outer end of each said linear upper arm portion;

a linear lower arm portion extending downwardly and slightly inwardly from each said downwardly curved elbow portion and terminating in a sharpened point at its free end;

wherein initial descent of said staple driving die from its raised towards its lowered position effects reformation upon the central concave portion of said concaved back portion of said staple to straighten said back portion prior to penetration of the sharpened points into epidermal tissue; and wherein the the further descent of said staple driving die toward its lowered position effects geometrical reformation and thereby implantation of the lower arm portions of said staple, by virtue of directing bending moments into the back portion of said staple adjacent the side edges of said anvil and thus forming shoulder regions at each end of the central back portion, such that the reformed configuration of said staple includes a central back portion and opposing downwardly diverging upper arm portions and opposing downwardly converging lower arm portions, which lower arm portions are implanted into the skin of a patient in a substantially linear path during said geometrical reformation, such that the tissue is neither gathered or bunched by the implanting staple and such that in its final implanted position, said staple substantially resembles a hexagon with one open side, said open side being defined between the opposed sharpened points of said implanted lower arm portions.

6. Surgical staple element applicator, comprising:

a body adapted to be hand-held and having a forward end;

said body forming a stapling station at said forward end;

a staple-holding magazine mounted with said body for feeding a staple blank into position for reforming and implanting into the skin of a patient;

a staple driving die, said body having driving die mount means mounting said staple driving die for movement between raised and lowered positions, said driving die including pushing means for engaging and reforming said staple blank to a final substantially hexagonal configuration;

an anvil means for receiving a staple blank from said staple-holding magazine for engagement by said driving die pushing means;

said body including anvil mount means mounting said anvil means for movement between release and work positions;

a displaceable trigger assembly and trigger mount means mounting said displaceable trigger assembly with said body for pivotal movement, said displaceable trigger assembly being operably attached to said staple driving die for moving said staple driving die between said raised and lowered position in order to reform said staple blank into a substantially hexagonal configuration;

adjustment means for adjusting the movement of said staple driving die to an adjusted lowered position in order to selectively adjust the final degree of bending of said staple in said substantially hexagonal configuration;

said adjustment means including an adjustable stop component mounted with said body; and stop component mount means mounting said adjustable stop component with said stapler body for permitting said staple driving die to move to an adjusted lowered position.

7. The structure set forth in claim 6, including:
said adjustable stop component being mounted for engagement by said pivotally displaceable trigger assembly whereby the adjustment of the pivotal displacement of said trigger assembly is controlled by abutment against said adjustable stop component.

8. The structure set forth in claim 6, including:
said adjustable stop component and said stop component mount means mounting said adjustable stop component with said body for selective movement between various positions wherein said displaceable trigger assembly engages said adjustable stop component in said various positions thereby controlling the degree of pivotal movement of said displaceable trigger assembly which correspondingly determines the limit of movement of said staple driving die and thus the degree of reformation of said staple in said substantially hexagonal configuration.

9. The structure set forth in claim 6, wherein:
said adjustable stop component comprises an adjustable slide and said stop component mount means mounts said adjustable slide for travel in said slot in said stapler body, said slide having an upper portion and a lower pad portion, wherein said adjustable slide is retained in selected positions along said slot, and said pad portion controlling pivotal movement of said displaceable trigger assembly by abutment therewith.

10. The structure set forth in claim 6, wherein said anvil means further includes:
an anvil plate;
said anvil mount means mounting said anvil plate for pivotal movement between said release and work positions;
said anvil plate including staple blank holding means for receiving said staple blank and retaining said staple blank in position for engagement by said staple driving die such that said staple driving die reforms said staple to a final substantially hexagonal configuration.

11. The structure set forth in claim 10, wherein said anvil plate includes:
an anvil lip formed with said anvil plate and a staple element receiving groove formed with said anvil plate, said staple blank receiving groove registering with a staple blank from said staple-holding magazine with said anvil plate in said work position, said staple blank receiving groove restraining said staple blank in position such that said staple blank is reformed over said anvil lip by said staple driving die during movement from said raised to said lowered position.

12. The structure set forth in claim 6, including:
said staple driving die and said anvil means having cooperating cam means for inter-engagement for pivoting said anvil means between said release and said work positions in response to movement of said staple driving die between said raised and said lowered positions.

13. The structure set forth in claim 12, including:
said staple driving die including spaced pusher elements which form said pusher means, said pusher elements being positioned on either side of said anvil lip with said anvil plate in said work position and said driving die in said lowered position.

14. The structure set forth in claim 13, including:
said pusher elements of said driving die having radiused cammed faces adapted to engage and reform said staple blank about said anvil lip for implanting said staple element.

15. The structure set forth in claim 6, including:
said staple driving die having upper and lower bearing surfaces;
said anvil means including an anvil plate having upper and lower cam surfaces which cooperate with said upper and lower bearing surfaces of said staple driving die whereby said anvil plate is pivoted between said release and work positions in response to movement of said driving die between said raised and lowered positions.

16. The structure set forth in claim 6, including:
said displaceable trigger assembly includes a trigger element and trigger mount means mounted with said body mounting said trigger element for pivotal movement; and
resistance means mounted with said trigger element for engaging said body to provide a biasing force against movement of said trigger.

17. Surgical staple element applicator, comprising:
a body adapted to be hand-held and having a forward end;
said body forming a stapling station at said forward end;
a staple-holding magazine mounted with said body for feeding a staple blank into position for reforming and implanting into the skin of a patient;
a staple driving die, said body having driving die mount means mounting said staple driving die for movement between raised and lowered positions, said driving die including pushing means for engaging and reforming said staple blank to a final substantially hexagonal configuration;
an anvil means for receiving a staple blank from said staple-holding magazine for engagement by said driving die pushing means;
said body including anvil mount means mounting said anvil means for movement between release and work positions;
a displaceable trigger assembly and trigger mount means mounting said displaceable trigger assembly with said body for pivotal movement, said displaceable trigger assembly being operably attached to said staple driving die for moving said staple driving die between said raised and lowered position in order to reform said staple blank into a substantially hexagonal configuration;

said displaceable trigger assembly includes a trigger element and trigger mount means mounted with said body mounting said trigger element for pivotal movement;

resistance means mounted with said trigger element for engaging said body to provide a biasing force against movement of said trigger;

said resistance means including a cantilevered leaf spring extending from said trigger element within said body; and said body including a plurality of obstructions which, upon engagement by said leaf spring, vary the spring resistance of said leaf spring and said trigger element attached to said leaf spring against further movement.

18. The structure set forth in claim 17, including:
said body including a series of obstructions mounted for engaging said spring resistance means in order to provide stepped forces of resistance against pivotal movement of said trigger element.

19. The structure set forth in claim 17, including:
said driving die mount means mounting said staple driving die for movement includes opposed channels formed with said body;
said staple driving die including a staple driving die plate which is mounted within said opposed channels for slideable movement between said raised and lowered positions, said driving die plate being attached to said displaceable trigger assembly for linear, slideable movement in said opposed channels in response to pivotal movement of said displaceable trigger assembly.

20. The structure set forth in claim 17, including:
said driving die plate having an opening therein to receive a portion of said anvil means with said anvil means in said work position.

21. Surgical staple element applicator, comprising:
a body adapted to be hand-held and having a forward end;
said body forming a stapling station at said forward end;
a staple-holding magazine mounted with said body for feeding a staple blank into position for reforming and implanting into the skin of a patient;
a staple driving die, said body having driving die mount means mounting said staple driving die for movement between raised and lowered positions, said driving die including pushing means for engaging and reforming said staple blank to a final substantially hexagonal configuration;
an anvil means for receiving a staple blank from said staple-holding magazine for engagement by said driving die pushing means;
said body including anvil mount means mounting said anvil means for movement between release and work positions;
a displaceable trigger assembly and trigger mount means mounting said displaceable trigger assembly with said body for pivotal movement, said displaceable trigger assembly being operably attached to said staple driving die for moving said staple driving die between said raised and lowered position in order to reform said staple blank into a substantially hexagonal configuration;
a forceps means mounted with said body and including pad elements for engaging the skin of a patient to facilitate selective approximation of wound edges prior to insertion of said staple blank, said forceps means being actuated by complementary engaging means with said staple driving die to move said pad element between an initial diverged rest position and a subsequent converged work position in response to movement of said staple driving die from said raised towards said lowered position whereby when converged, position of said pad elements remain stationary during further movement of said staple driving die towards said lowered position, in order to maintain said wound approximation during the implantation sequence of said staple.

22. The structure set forth in claim 21, including:
said staple driving die includes forceps actuating means for engaging and converging said forceps pad elements during travel of said staple driving die from said initial to a first intermediate position.

23. The structure set forth in claim 22, wherein:
said staple driving die and said anvil means having inter-engaging cooperating cam means for pivoting said anvil means between said release and said work positions in response to movement of said staple driving die between said raised and a second intermediate position.

24. The structure set forth in claim 23, wherein:
said staple driving die pushing means engages and reforms said staple blank during travel of said driving die from said second intermediate position to said lowered position.

25. The structure set forth in claim 24, including:
adjustment means for selectively controlling the distance of movement of said staple driving die from said lowered position to said adjusted lowered position.

26. The structure set forth in claim 24, including:
said displaceable trigger assembly includes a trigger element and trigger mount means mounted with said body mounting said trigger element for pivotal movement; and
spring resistance means mounted with said trigger element for engaging said body to provide a biasing force against movement of said trigger.

27. The structure set forth in claim 26, including:
said body including a series of obstructions mounted for engaging said spring reistance means in order to provide stepped forces of resistance against pivotal movement of said trigger element.

28. The structure set forth in claim 27, including:
said spring resistance means including a cantilevered leaf spring extending from said trigger element within said body;
said body including a plurality of obstructions which, upon engagement by said leaf spring, vary the spring resistance of said leaf spring and said trigger element attached to said leaf spring against further movement.

29. The structure set forth in claim 27, including:
said spring resistance means engaging one of said obstructions to provide a first level of resistance during movement of said staple driving die from said raised position to said second intermediate position for converging said forceps means, and pivoting said anvil means from said release to said work position.

30. The structure set forth in claim 29, including:

said spring resistance means engaging another of said obstructions to provide a second level of resistance during movement of said staple driving die from said second intermediate position to said lowered position.

31. The structure set forth in claim 30, including:
said spring resistance means engaging another of said obstructions to provide a third level of resistance during movement of said staple driving die from said lowered to said adjusted lowered position as a result of said adjustments means adjusting the lowered position of said driving die.

32. The structure set forth in claim 24, including:
adjustment means for adjusting the movement of said staple driving die in order to adjust said lowered position of said driving die to thereby adjust the final degree of reformation of said staple in said substantially hexagonal configuration.

33. The structure set forth in claim 32, wherein said adjustment means includes:
an adjustable stop component; and
stop component mount means mounting said adjustable stop component with said stapler body for permitting the movement of said staple driving die to said adjusted lowered position.

* * * * *

UNITED STATES PATENT AND TRADEMARK OFFICE
CERTIFICATE OF CORRECTION

PATENT NO. : 4,887,756

DATED : December 19, 1989

INVENTOR(S) : David P. Puchy

It is certified that error appears in the above-identified patent and that said Letters Patent is hereby corrected as shown below:

In column 1, line 22, change "relay" to --rely--.
In column 2, line 5, following the word "costly" insert --.--.
In column 2, line 6, following the words "Just as" insert --he--.
In column 2, lines 9-10, change "practive" to --practice--.
In column 3, line 3, following the word "apposition" insert --or--.
In column 3, line 31, following the word "which" insert --can--.
In column 3, line 51, following the word "many" insert --parts--.
In column 4, line 9, following the word "reformation" insert --,--.
In column 4, line 39, delete "or reformed" and insert therefor --deformed--.
In column 5, line 29, following the word "prong" delete --forming--.
In column 6, line 1, delete the word "and" and substitute therefor --the--.
In column 6, line 32, following the word "preformed" insert --staple--;
    delete the word "eliment" and insert therefor --element--.
In column 6, line 58, delete the word "opposition" and insert therefor
    --apposition--.
In column 6, line 61, delete the word "emplantation" and insert therefor
    --implantation--.
In column 6, line 51, change "drive" to --driving--.
In column 7, line 35, following the word "position" insert
    --to draw together--.
In column 8, line 5, change "perpendicular" to --perpendicularly--;
    change "of" to --or--.
In column 8, line 52, delete "FIG. 13" and substitute therefor --FIG. 14--.
In column 8, line 53, change "staple or preferred" to --stapler and preformed--.
In column 8, line 1, delete the word "with" and substitute therefor
    --which--.
In column 10, line 32, delete the word "separated" and insert therefor
    --serrated--.
In column 12, line 28, delete the word "of" and insert therefor --or--.
In column 13, line 45, delete the word "patient" and insert therefor
    --salient--.
In column 14, line 6, delete the word "chatching" and insert therefor
    --notching--.

UNITED STATES PATENT AND TRADEMARK OFFICE
CERTIFICATE OF CORRECTION

PATENT NO. : 4,887,756

DATED : December 19, 1989

INVENTOR(S) : David P. Puchy

It is certified that error appears in the above-identified patent and that said Letters Patent is hereby corrected as shown below:

In column 14, line 18, delete the word "repoitioning" and insert therefor --repositioning--.
In column 14, line 35, delete the word "would" and insert therefor --wound--.
In column 14, line 48, delete the word "thes" and insert therefor --the--.
In column 15, line 7, following the word "reached" delete the word --to--.
In column 15, line 14, after "necessary" insert --,--.

In claim 1, line 49, delete the word "staple-hold" and insert therefor --staple-holding--.
In claim 5, line 29, change "the the" to --the--.
In claim 5, line 51, delete the word "patent" and insert therefor --patient--.
In claim 21, line 5, delete the word "eliment" and insert therefor --element--.
In claim 27, line 48, delete the word "reistance" and insert therefor --resistance--.

Signed and Sealed this

Twenty-fifth Day of June, 1991

*Attest:*

HARRY F. MANBECK, JR.

*Attesting Officer*  *Commissioner of Patents and Trademarks*